US007033804B2

(12) United States Patent
Dodge et al.

(10) Patent No.: US 7,033,804 B2
(45) Date of Patent: Apr. 25, 2006

(54) METHODS FOR THE PRODUCTION OF PRODUCTS IN HOST CELLS

(75) Inventors: Timothy C. Dodge, Sunnyvale, CA (US); Fernando Valle, Burlingame, CA (US)

(73) Assignee: Genencor International, Inc., Palo Alto, CA (US)

( * ) Notice: Subject to any disclaimer, the term of this patent is extended or adjusted under 35 U.S.C. 154(b) by 83 days.

(21) Appl. No.: 10/116,821

(22) Filed: Apr. 4, 2002

(65) Prior Publication Data

US 2003/0040086 A1    Feb. 27, 2003

Related U.S. Application Data

(60) Provisional application No. 60/282,277, filed on Apr. 5, 2001, provisional application No. 60/281,571, filed on Apr. 4, 2001.

(51) Int. Cl.
*C12P 7/60* (2006.01)
*C12P 7/58* (2006.01)

(52) U.S. Cl. ...................................... 435/138; 435/137
(58) Field of Classification Search ................ 435/137, 435/138, 193, 455, 463, 471, 477
See application file for complete search history.

(56) References Cited

U.S. PATENT DOCUMENTS

| | | | |
|---|---|---|---|
| 4,757,012 A | 7/1988 | Estell et al. | 435/172.3 |
| 4,758,514 A | 7/1988 | Light et al. | 435/91 |
| 4,760,025 A | 7/1988 | Estell et al. | 435/222 |
| 4,767,870 A | 8/1988 | Fujiwara | 549/315 |
| 5,004,690 A | 4/1991 | Light et al. | 435/138 |
| 5,008,193 A | 4/1991 | Anderson et al. | 435/138 |
| 5,032,514 A | 7/1991 | Anderson et al. | 435/138 |
| 5,240,843 A | 8/1993 | Gibson et al. | 435/188 |
| 5,272,073 A | 12/1993 | Frost et al. | 435/155 |
| 5,376,544 A | 12/1994 | Lazarus et al. | 435/190 |
| 5,583,025 A | 12/1996 | Lazarus et al. | 435/190 |
| 5,686,286 A | 11/1997 | Fisher | 435/199 |
| 5,747,306 A | 5/1998 | Oka | 435/138 |
| 5,795,761 A | 8/1998 | Powers et al. | 435/190 |
| 5,939,307 A | 8/1999 | Wang et al. | 435/252.33 |
| 5,985,617 A | 11/1999 | Liao | 435/72 |
| 6,025,184 A | 2/2000 | Laffend et al. | 435/252.33 |

FOREIGN PATENT DOCUMENTS

| | | |
|---|---|---|
| EP | 0 955 368 A2 | 11/1999 |
| EP | 1 087 015 A2 | 3/2001 |
| WO | WO 92/18637 | 10/1992 |
| WO | WO 98/21340 | 5/1998 |
| WO | WO 98/59054 | 12/1998 |
| WO | WO 99/28480 | 6/1999 |
| WO | WO 99/55877 | 11/1999 |
| WO | WO 99/61623 | 12/1999 |
| WO | WO 01/12833 | 2/2001 |
| WO | WO 02/081631 | 4/2002 |
| WO | WO 02/081440 | 10/2002 |

OTHER PUBLICATIONS

ATCC Bacteria and Bacteriophages, 19th Edition, 1996, p. 260.*
Lavine et al. (1982) Mol Cell Biochem 48:45-58.*
Branden et al. "Introduction to Protein Structure", Garland Publishing Inc., New York, 1991, p. 247.*
Dodge et al. (2001) Abstracts of Papers—American Chemical Society, 221st, BIOT-263.*
Waleron et al. (2002) Microbiol 148 :583-595.*
Seffernick et al. (1999) J Bacteriol 183:2405-2410.*
Barredo et al. "Glucokinase-Deficient of *Penicillium chrysogenum* Is Derepressed on Glucose Catabolite Regulation of Both β-Galactosidase and Penicillium Biosynthesis," Antimicrob. Agents-Chemother 32: 1061-1067, (1988).
Bouvet, et al. "Taxonomic Diversity of the D-Glucose Oxidation Pathway in the *Enterobacteriaceae*," International Journal of Systematic Bacteriology, 39:61-67, (1989).
Braun et al. "Immunogenic Duplex Nucleic Acids are Nuclease Resistant," J. Immunol. 141: 2084-9, (1988).
Cha et al, "Identification and Characterization of a *Pantoea citrea* Gene Encoding Glucose Dehydrogenase That Is Essential for Causing Pink Disease of Pineapple," Appl. Environ. Microbiol 63(1), 71-76 (1997).

(Continued)

*Primary Examiner*—David J. Steadman
(74) *Attorney, Agent, or Firm*—Lynn Marcus-Wyner

(57) ABSTRACT

The invention provides methods and host cells for the production of ascorbic acid intermediates. The invention also provides host cells having a modification in a polynucleotide that uncouples the catabolic pathway from the oxidative pathway by deleting the encoding for an endogenous enzymatic activity that phosphorylates D-glucose at its 6th carbon and/or a polynucleotide that has deleted the encoding for endogenous enzymatic activity that phosphorylates D-gluconate at its 6th carbon. Such host cells are used for the production of products, such as, ascorbic acid intermediates. Nucleic acid and amino acid sequences with inactivated enzymatic activity which phosphorylates D-glucose at its 6th carbon and inactivated enzymatic activity which phosphorylates D-gluconate at its 6th carbon are provided.

16 Claims, 19 Drawing Sheets

OTHER PUBLICATIONS

Chaturvedi et al. "Stabilization of triple-stranded oligonucleotide complexes: use of probes containing alternating phosphodiester and stereo-uniform cationic phosphoramidate linkages," Nucleic Acids Res. 24: 2318-23, (1996).

DiMarco et al "D-Glucose Transport System of *Zymomonas mobilis*," Appl. Environ. Microbiol. 49:151-157, (1985).

Flores et al., "Pathway engineering for the production of aromatic compounds in *Escherichia coli*," Nat. Biotechnol. 14: 620-623, (1996).

Frey et al., The Molecular biology of IncQ plasmids. In: Thomas (Ed.), Promiscuous Plasmids of Gram Negative Bacteria. Academic Press, London, pp. 79-94, (1989).

Frey et al., "Replication and copy number control of the broad-host-range plasmid RSF1010," Gene 113:101-106, (1992).

Frohlich et al., "The primary structure of the years hexokinase Pll gene (HXK2) which is responsible for glucose repression," Gene 36:105-111, (1985).

Fukuda et al., "Cloning of the Glucokinase Gene in *Escherichia coli B*" J. Bacteriol. 156:922-925, (1983).

Gerhardt, Philipp et al., ed., "Manual of Methods for General Bacteriology," editor-in-chief R. G. E. Murray, editor, Morphology, Washington, D. C.: American Society for Microbiology, pp. 210-213, (1981).

Grindley et al., "Conversion of Glucose to 2-Keto-L-Gluconate, an Intermediate in L-Ascorbate Synthesis, by a Recombinant Strain of *Ervinia citreus*," Applied and Environmental Microbiology 54: 1770-1775, (1988).

Harrod et al., " Derepressed utilization of L-malic acid and succinic acid by mutants of *Pachysolen tannophilus*," J. Ind. Microbiol. Biotechnol. 18:379-383, (1997).

Hoess et al., "Mechanism of Strand Cleavage and Exchange In the Cre-lox Site-specific Recombination System," J. Mol. Biol., 181:351-362, 1985.

Hoess et al., "Mechanism of Strand Cleavage and Exchange In the Cre-lox Site-specific Recombination System," J. Mol. Biol., 181:351-362, 1985.

Kageyama et al. "*Pantoea punctata* sp. nov., *Pantoea citrea* sp. nov., and *Pantoea terra* sp. nov. isolated from Fruit and Soil Samples," International Journal of Systematic Bacteriology vol. 42, p. 203-210, (1992).

Kramer et al., "The gapped duplex DNA to oligonucleotide-directed mutation construction," Nucleic Acids Res. 12:9441, (1984).

Kulbe et al. "Enzyme-Catalyzed Production of Mannitol and Gluconic Acid," Ann. N.Y. Acad Sci 6:552, (Los Angeles), (1987).

Latimer et al. "Specificity of Monoclonal Antibodies Produced against Phosphorothioate and Ribo Modified DNAs," Molec. Immunol. 32:1057-1064, (1995).

Lin E.C. C., "Glycerol Dissimilation and its regulation In bacteria," Ann. Rev. Microbiol., 30:535-578, (1976).

Matsushita et al., "Membrane-Bound D-Gluconate Dehydrogenase from," J. Biochem. 85:1173-1181, (1979).

Miller et al., "A Novel Suicide Vector and Its Use in Construction of Insertion Mutations: Osmoregulation of Outer Membrane Proteins and Virulence Determinants in *Vibrio cholerae* Requires toxR," J. Bacteriol. 170, 2575-2583, (1988).

Neijssel et al., "Physiological Significance and Bioenergetic Aspects of Glucose Dehydrogenase," Antonie Van Leauvenhoek, 56(1):51-61, 1989.

Pachla et al, "Determination of Ascorbic Acid in Foodstuffs, Pharmaceuticals, and Body Fluids by Liquid Chromatography with Electrochemical Detection," Anal. Chem. 48:364, (1976).

Palmeros et al., "A family of removable cassettes designed to obtain antibiotic-resistance-free genomic modifications of *Escherichia coli* and other bacteria," Gene 247, 255-264, (2000).

Parker et al., "Characterization of the *Zymomonas mobilis* glucose facilitator gene product (glf) in recombinant *Escherichia coli*: examination of transport mechanism, kinetics and the role of glucokinase in glucose transport," Mol. Microbiol. 15: 795-802, (1995).

Peyrottes et al., "Oligodeoxnucleoside phosphoramidates (P-$NH_2$): synthesis and thermal stability of duplexes with DNA and RNA targets," Nucleic Acids Res. 24: 1841-8, (1996).

Pujol et al, "gdhB, a gene encoding a second quinoprotein glucose dehydrogenase in *Pantoea citrea*, is required for pink disease of pineapple," Microbiol. 145, 1217-1226, (1999).

Pujol, et al, "Genetic and Biochemical Characterization of the Pathway in *Pantoea citrea* Leading to Pink Disease of Pineapple," J. of Bacterial. 182(8), 2000.

Reichstein and Grussner, "Eine ergiebige Synthese der I-Ascorbinasure (C-Vitamin)$^2$)," Helv. Chem. Acta., 17, 311-328 (1934).

Russell et al "Carbohydrate Metabolism in the Mosquito Pathogen *Bacillus sphaericus 232*," Appl. Environ. Microbiol., 55: 294-297, (1989).

Schultz et al. "Oligo-2'-fluoro-2'-deoxynucleotide N3'-P5' phosphoramidates: synthesis and properties," Nucleic Acids Res. 24: 2966-73, (1996).

Simons et al., "Aerobic 2-ketogluconate metabolism of *Klebsiella pneumoniae* NCTC 418 grown in chemostat culture," J. Gen. Microbiol., 137:1479, (1991).

Smith et al., "Purification and characterization of glucose dehydrogenase from the thermoacidophilic archaebacterium *Thermoplasma acidophilum*," Biochem. J., 261:973, (1989).

Stroshane et al., "Fermentation of Glucose by *Acetobacter melanogeuns*," Biotechnol. BioEng., 19(4) 459, (1977).

Wedlock, et al. "A Hexokinase Associated with Catabolite Repression in *Pachysolen tannophilus*," J. Gen. Microbiol. 135: 2013-2018, (1989).

Truesdell, et al., " Pathways for Metabolism of Ketoaldonic Acid in an *Erwinia* sp." Journal of Bacteriology, 173:6651-6656, (1991).

Walsh et al. "Cloning of genes that Complement Yeast Hexokinase and Glucokinase Mutants," J. Bacteriol. 154:1002-1004, (1983).

Wedlock, et al. "A Hexokinase Associated with Catabolite Repression in *Pachysolen tannophilus*," J. Gen. Microbiol. 135: 2013-2018, (1989).

Yum et al, "Cloning and Expression of a Gene Cluster Encoding Three Subunits of Membrane-Bound Gluconate Dehydrogenase from *Erwinia cypripedii* ATCC 29267 in *Escherichia coli*," J. of Bacteriol. 183(8): 2230-2237, (1997).

Copy of PCT Search Report for PCT/US02/10575, mailed Sep. 17, 2002.

Copy of PCT Search Report for PCT/US02/10949, mailed Jun. 12, 2003.

* cited by examiner

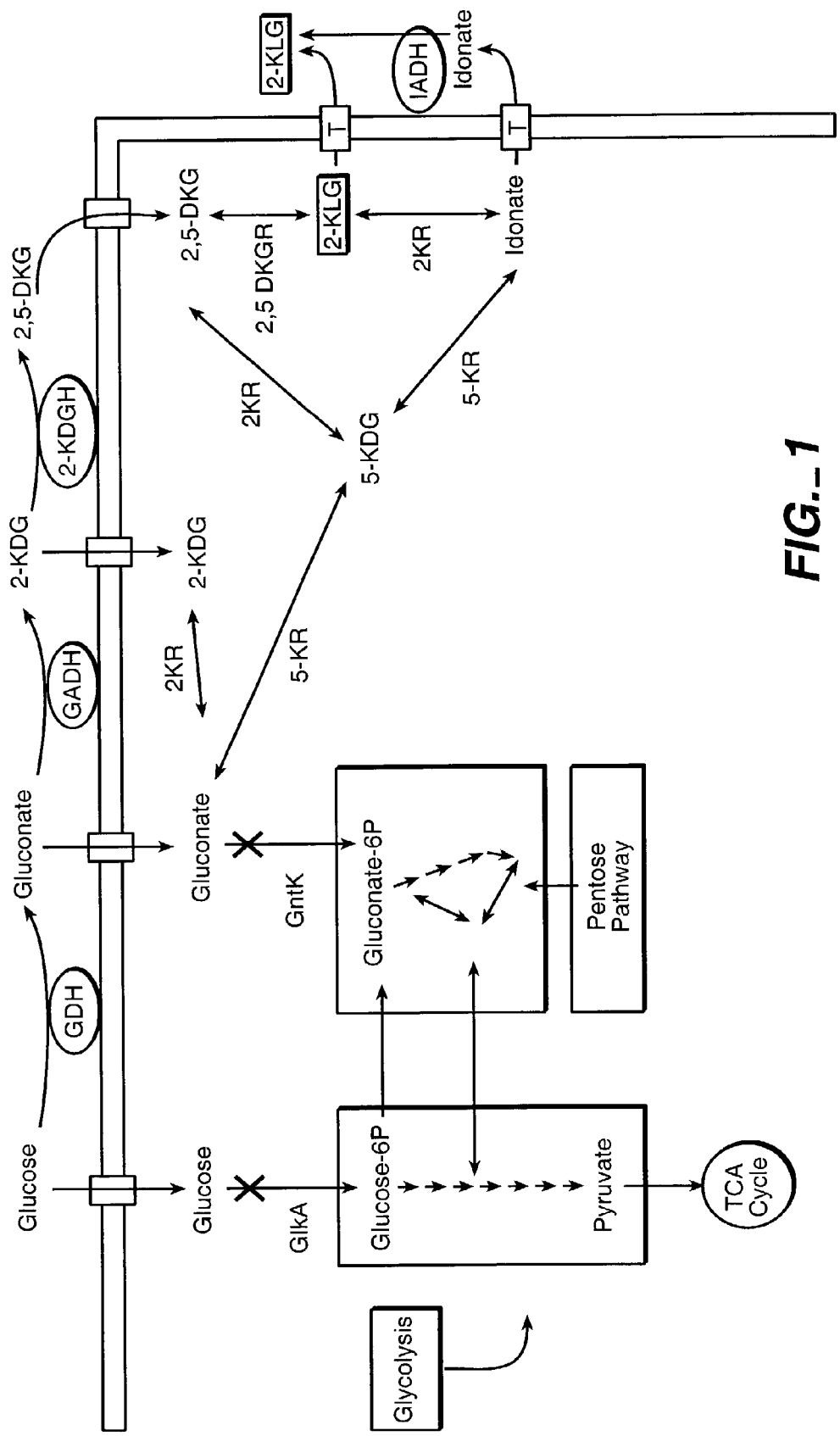
FIG._1

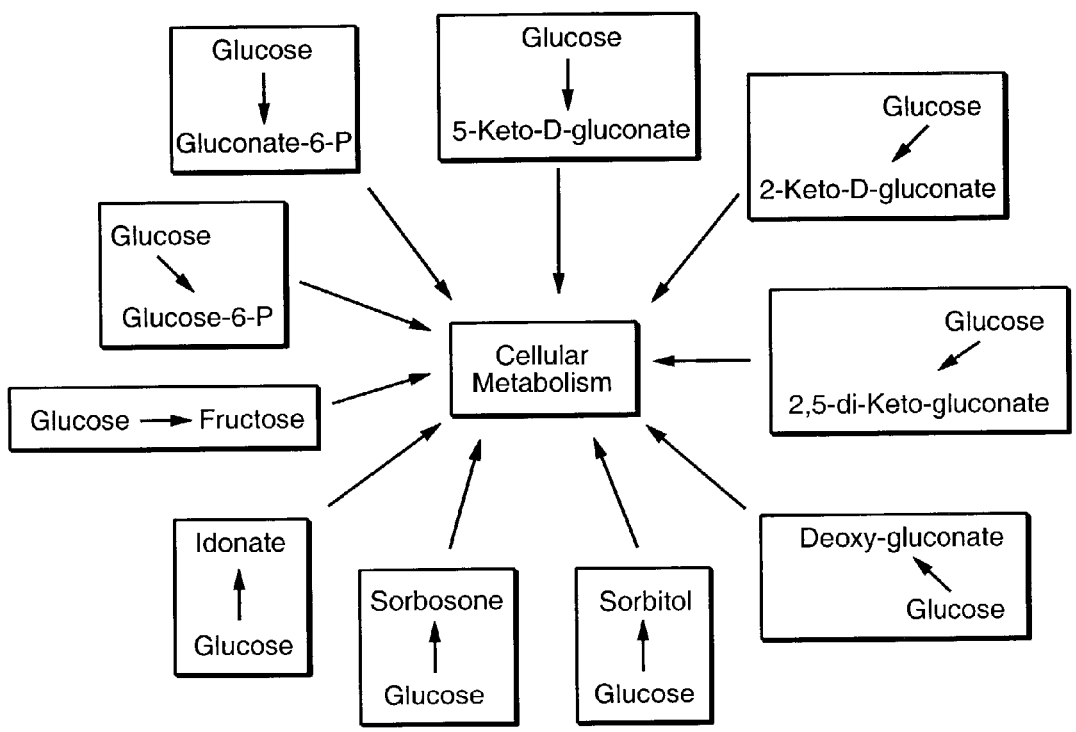
FIG._2

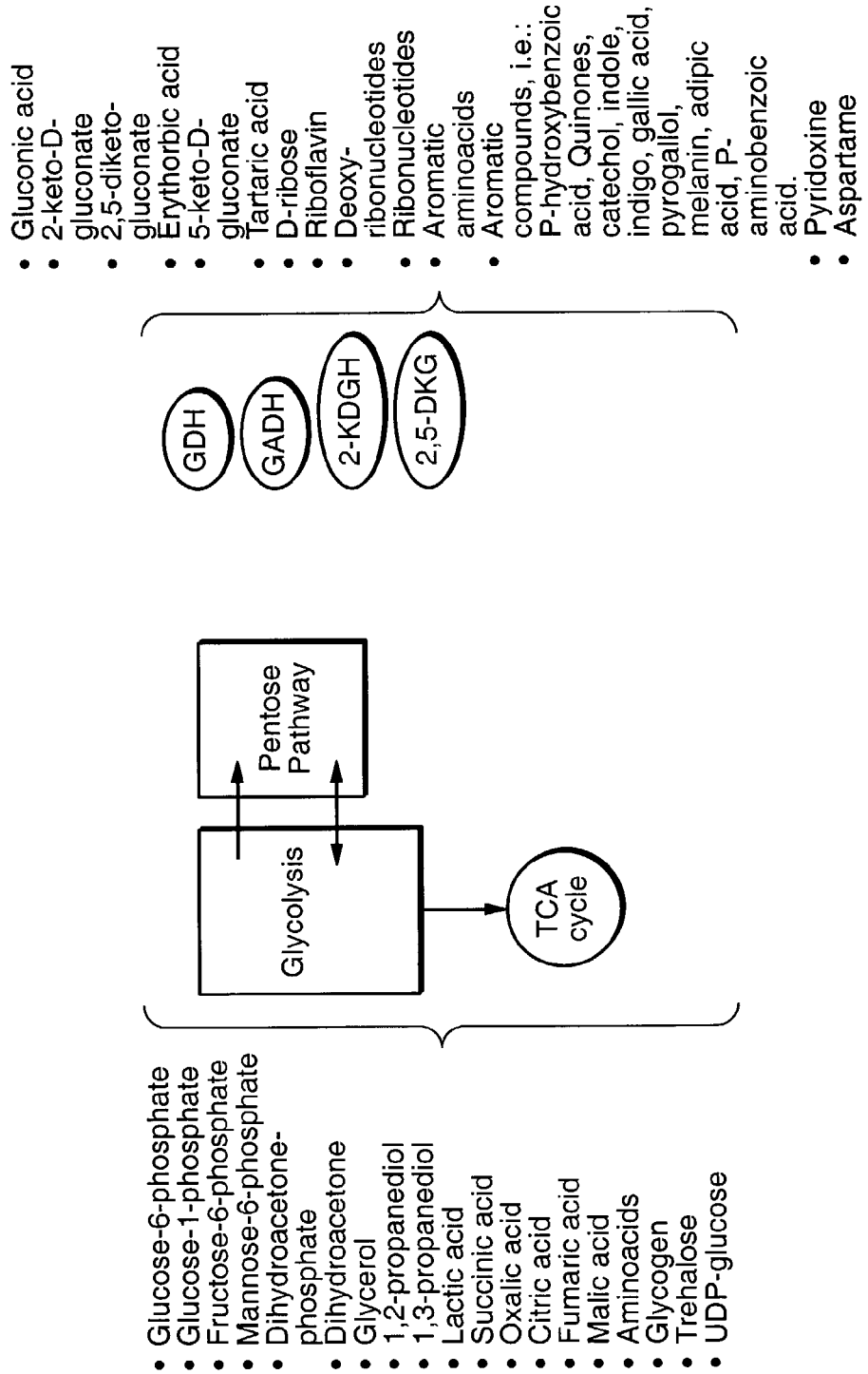
FIG._3

DNA sequence of the Glucokinase structural gene from *P. citrea*. The recognition site for the restriction enzymes NcoI (CCATGG) and SnaBI (TACGTA) are highlighted.

ATGACAAACTATGCCTTGGTCGGCGATGTAGGCGGAACTAACGCCCGCCTTGCGTTGTGT
GATGTGACTGACGGCAGCATCTCGCAGGCCAAAACCTTTTCAACCGAGGATTACCAGAGC
CTGGAAGATGTTATTCGTGAGTATCTGGCGGATCAACAAGCCATCACCTGTGCATCTATC
GCCATCGCCTGTCCGGTGAAAGATGACTGGATTGAAATGACTAATCATAGCTGGGCGTTC
TCTATCAGTGAGATGAAACAAAATCTCGGGCTGGAACATCTGGAAGTGATTAACGATTTC
ACTGCGGTCT<u>CCATGG</u>CAATTCCAATGCTGGGCAGTGACGATGTCATTCAGTTCGGCGGT
GGTGCACCGGTAAAAGATAAACCGATAGCTATCTATGGTGCCGGAACAGGACTGGGGGTG
AGCCATCTGGTTCATGTCAACAAACACTGGGTCAGCTTGCCTGGTGAAGGCGGACATGTA
GATTTCACCTGTGGTACCGAAGAAGAAGACATGATCATGAGTGTGCTGCGTGCAGAACGT
GGCCGGGTGTCAGCTGAACGGGTGCTGTCAGGAAAAGGTCTGGTGAATATTTACCGGGCC
ATTGTGATTTCTGACAACCGTGTTCCTGAACGTCTGCAACCTCAGGACGTAACCGAGCGT
GCATTATCCGGAAGCTGTACTGACTGTCGTCGTGCACTGTCATTGTTCTGTGTGATTATG
GGACGTTTTGGCGGGAACCTGGCCCTGACACTTGGAACCTTCGGTGGGGTGTATATTGCC
GGCGGAATTGTTCCACGCTTCCTGCAGTTCTTTAAAGCCTCCGGTTTCCGTGCTGCTTTC
GAAGATAAGGGACGTTTCCGTTCT<u>TACGTA</u>CAGGATATTCCGGTCTATCTGATTACCCAT
GATCAGCCGGGGCTGCTGGGTGCCGGTGCCCATATGCGCCAGACTTTAGGGATGGAACTG
TAA

*FIG._4*

Protein sequence of the Glucokinase gene from *P. citrea*.

MTNYALVGDVGGTNARLALCDVTDGSISQAKTFSTEDYQSLEDVIREYLADQQAITCASI
AIACPVKDDWIEMTNHSWAFSISEMKQNLGLEHLEVINDFTAVSMAIPMLGSDDVIQFGG
GAPVKDKPIAIYGAGTGLGVSHLVHVNKHWVSLPGEGGHVDFTCGTEEEDMIMSVLRAER
GRVSAERVLSGKGLVNIYRAIVISDNRVPERLQPQDVTERALSGSCTDCRRALSLFCVIM
GRFGGNLALTLGTFGGVYIAGGIVPRFLQFFKASGFRAAFEDKGRFRSYVQDIPVYLITH
DQPGLLGAGAHMRQTLGMEL

*FIG._5*

DNA sequence of the Gluconate kinase structural gene from P. citrea. The recognition site for the restriction enzyme Pst I (CTGCAG) is highlighted.

ATGAGTACAGCTTCTTCAAATCATCATGTGTTTATCCTGatgGGCGTTTCCGGCAGCGGA

AAGTCGGTGGTCGCCAATCGTGTCTCTTACCAGTTGCAAACCGCATTTCTTGATGGTGAC

TTTCTGCATCCCAGAGCGAACATCATGAAAATGGCTGACGGGCATCCGCTCAATGATCAG

GATCGTCAACCCTGG<u>CTGCAG</u>GCCATTAATGATGCGGCTTTTGCTATGCAGCGGACCCAG

GCTGTATCGTTAATTGTGTGTTCGTCACTGAAAAAAGTTATCGCGATATTCTTCGTGAA

GGTAACAGCAATCTTAAGTTTGTTTATCTGAAAGGTGACTTCGATACCATCGAATCGCGT

CTTAAAGCCCGCAAGGGACACTTCTTCAAACCCGCCATGCTGGTAACACAATTCGCAACT

CTCGAAGAGCCGACCCCGGATGAAACTGATGTCCTCACGGTGGATATCCGGCAGTCGCTG

GATGAGGTTGTTGCTGCCACGGTAGAAGCGATCAAACACGCAATTCAGTAA

FIG._6

Protein sequence of the Glucokinase gene from P. citrea.

MSTASSNHHVFILMGVSGSGKSVVANRVSYQLQTAFLDGDFLHPRANIMKMADGHPLNDQ
DRQPWLQAINDAAFAMQRTQAVSLIVCSSLKKSYRDILREGNSNLKFVYLKGDFDTIESR
LKARKGHFFKPAMLVTQFATLEEPTPDETDVLTVDIRQSLDEVVAATVEAIKHAIQ

SEQ ID NO: 5
Name: glk 30
5'-----TTTCAACCGAGGAGGATTACCAGAGC-----3'

SEQ ID NO: 6
Name: glk 31
5'-----CACGGCGCAGGAATGATACAGAGA-----3'

SEQ ID NO: 7
Name: gnt 1
5'-----GGGAAGGTTGCAGCGCGTGACCGC------3'

SEQ ID NO: 8
Name: gnt2
5'-----GCCGGTTGCAGCGCGTGACCGC-----3'

SEQ ID NO: 9
Name: pcgnt 3
5'-----ACTAAAAGGGTACGGTGTCAGAGA-----3'

SEQ ID NO: 10
Name: pcgnt 4
5'-----GTGTTGCGGTACTTATCATTATTA-----3'

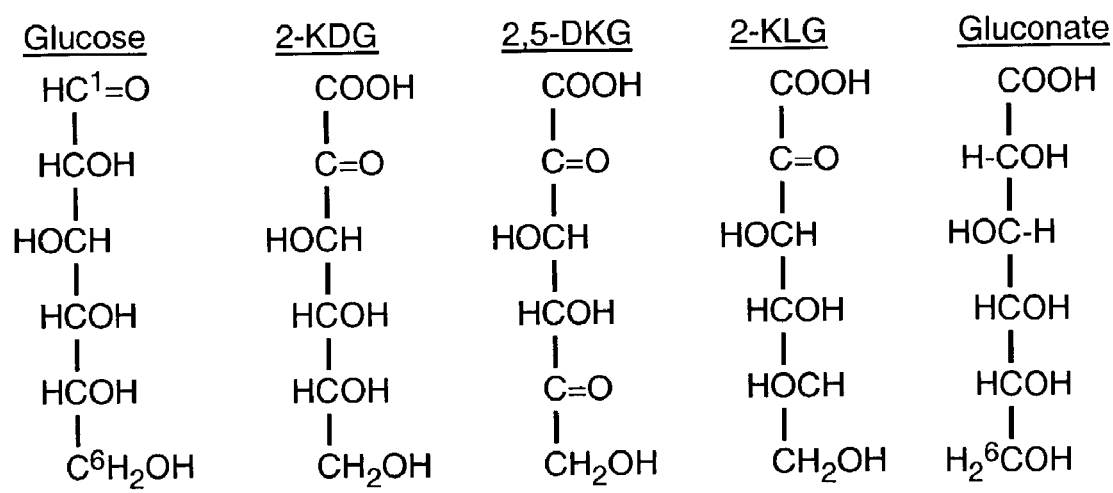
FIG._9

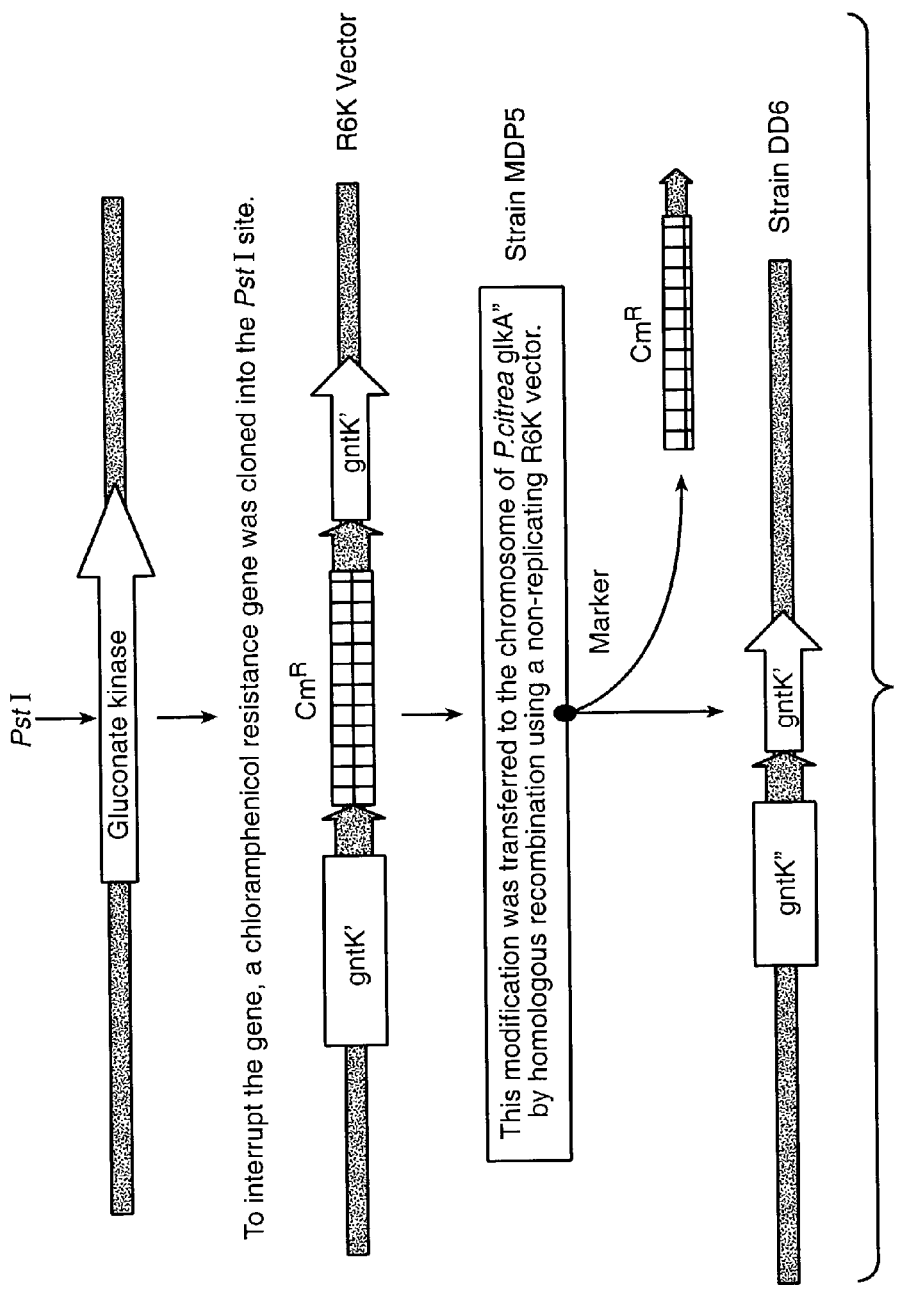
FIG._10

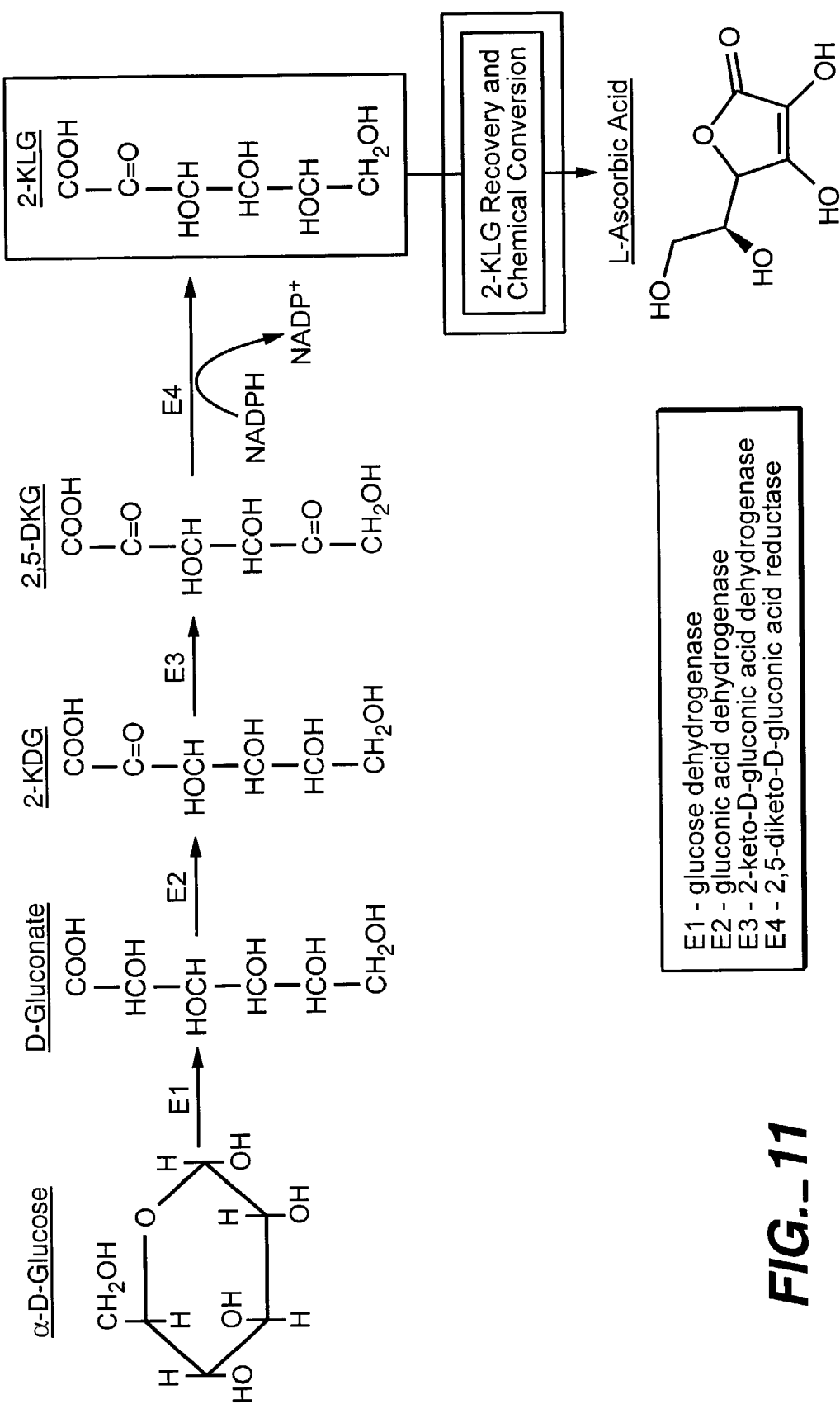
FIG._11

Net Reactions During Fermentation
- Glucose + 1.5 $O_2$ = DKG
- Glucose/Fructose = 6 $CO_2$ + 12 NAD(P)H
- DKG + NADPH = KLG + NADPH = Idonate
- DKG = 6 $CO_2$ + 9 NAD(P)H
- NAD(P)H + 0.5 $O_2$ = $H_2O$
- Glucose/Fructose + 0.732 $NH_3$ + 2.16 $O_2$ =
  3.66 Biomass + 2.34 $CO_2$ + 3.80 $H_2O$
FIG._12
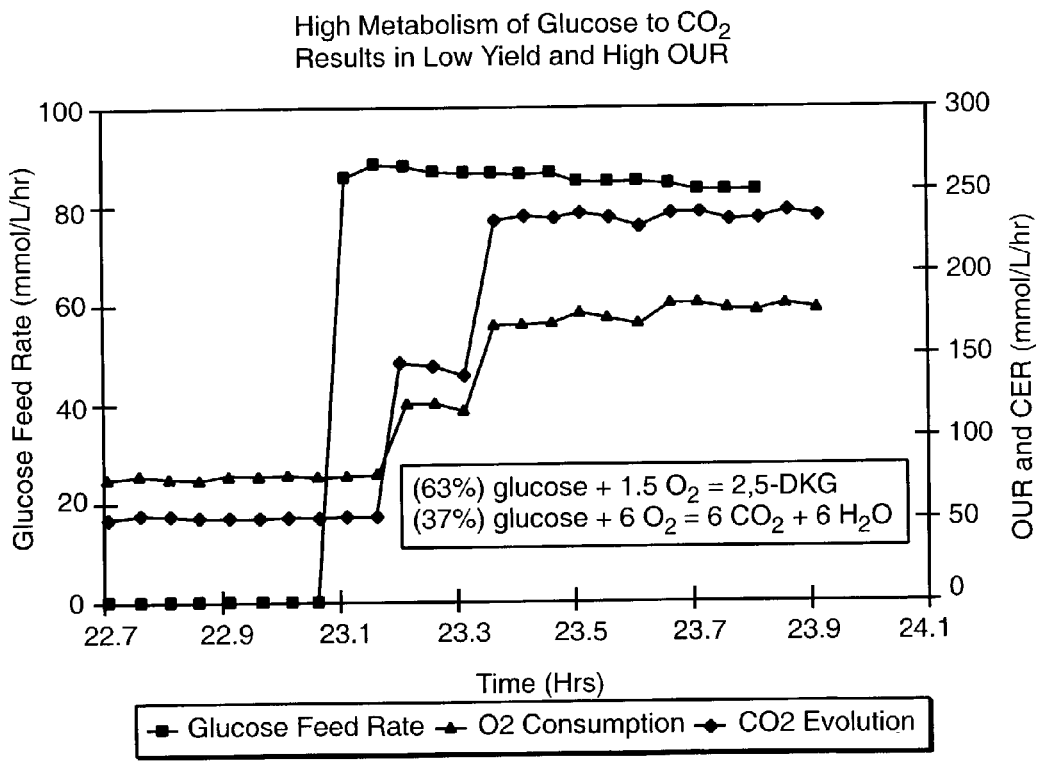
FIG._13

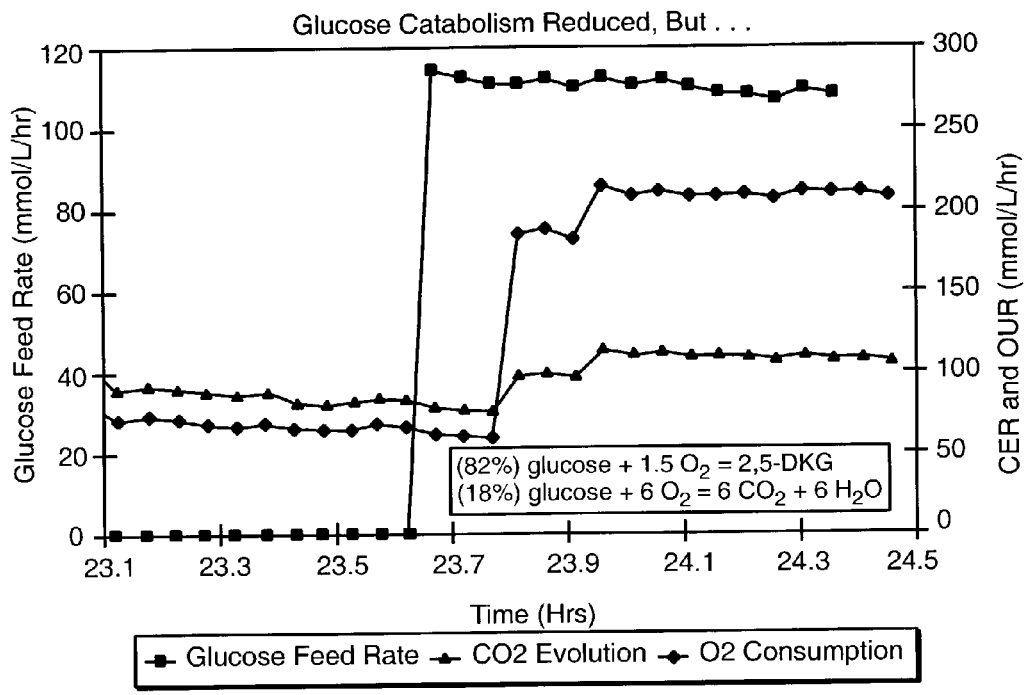
FIG._14
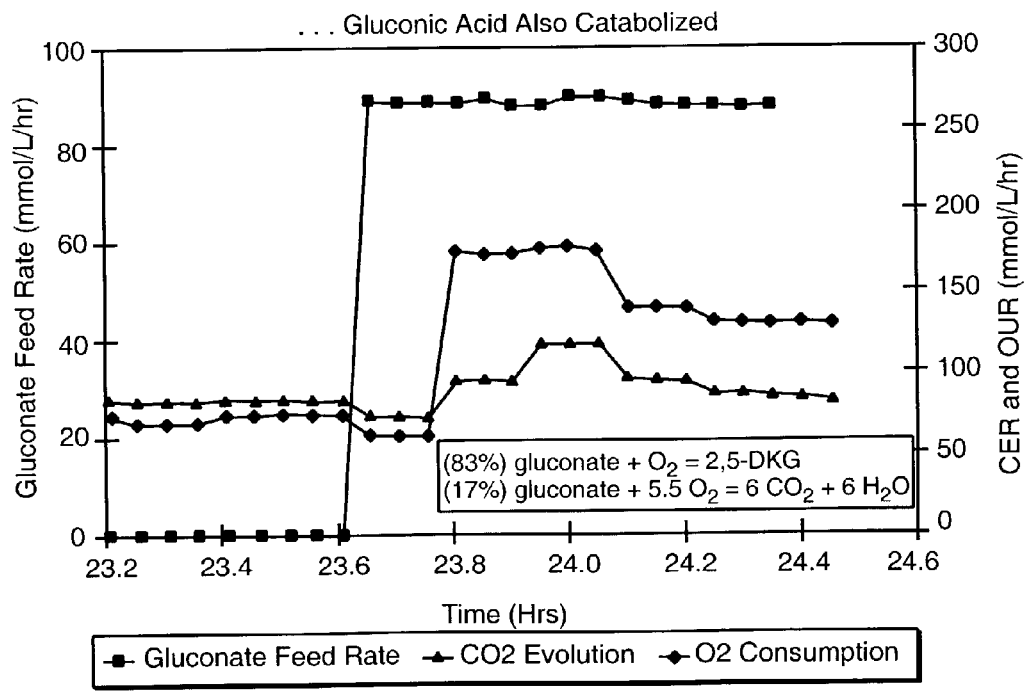
FIG._15

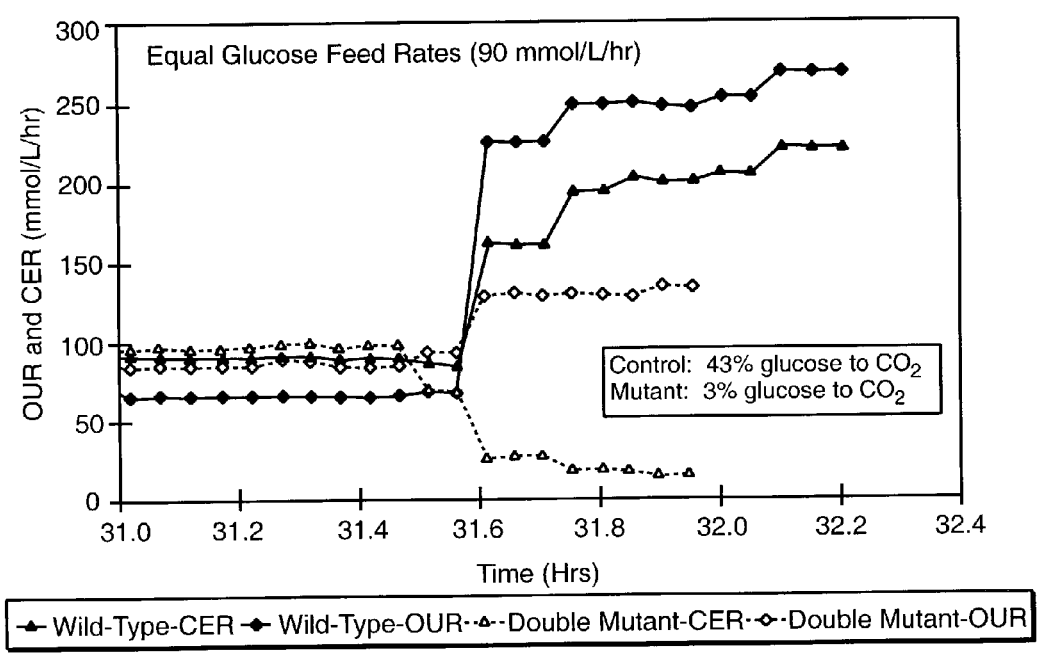
FIG._16

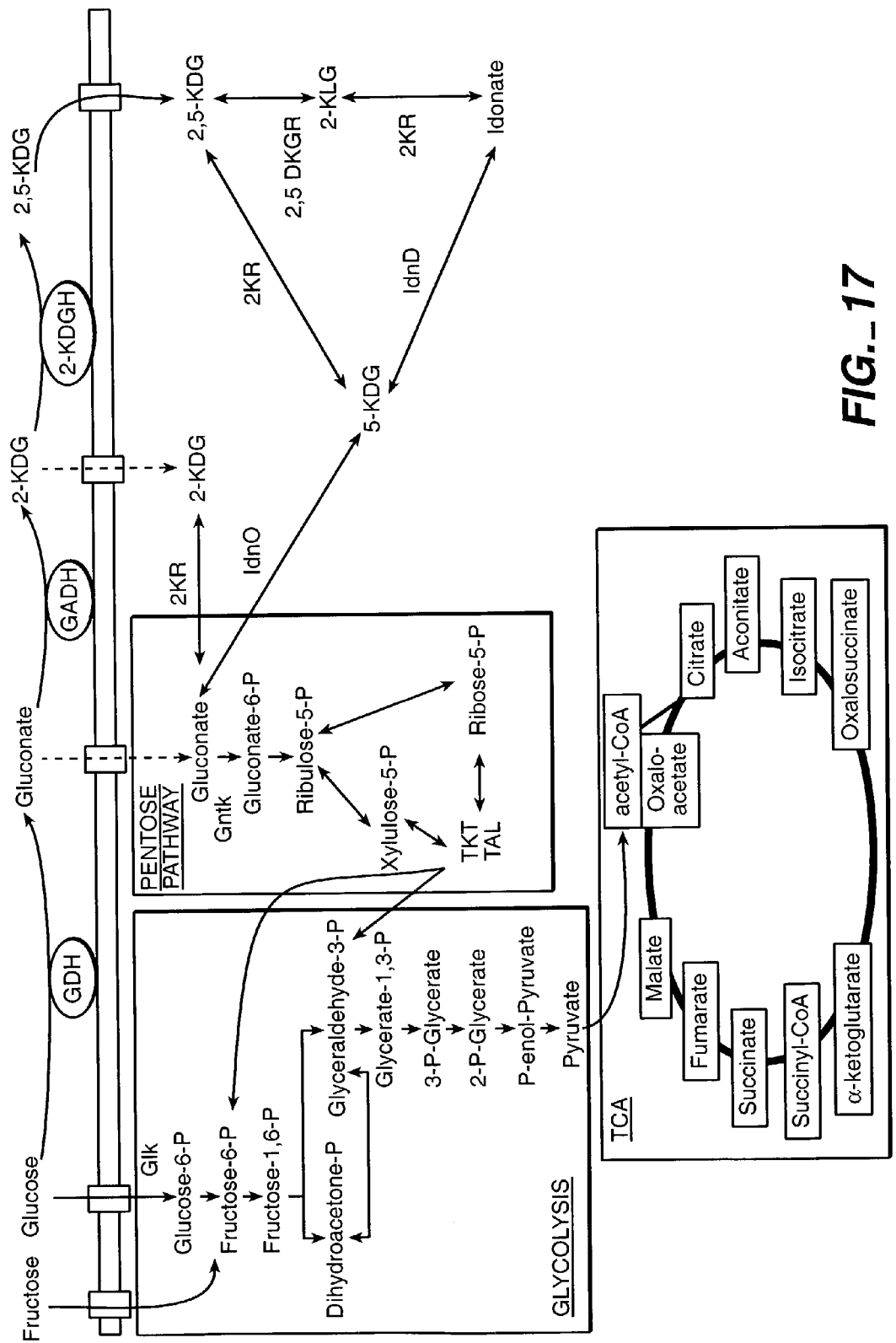
FIG._17

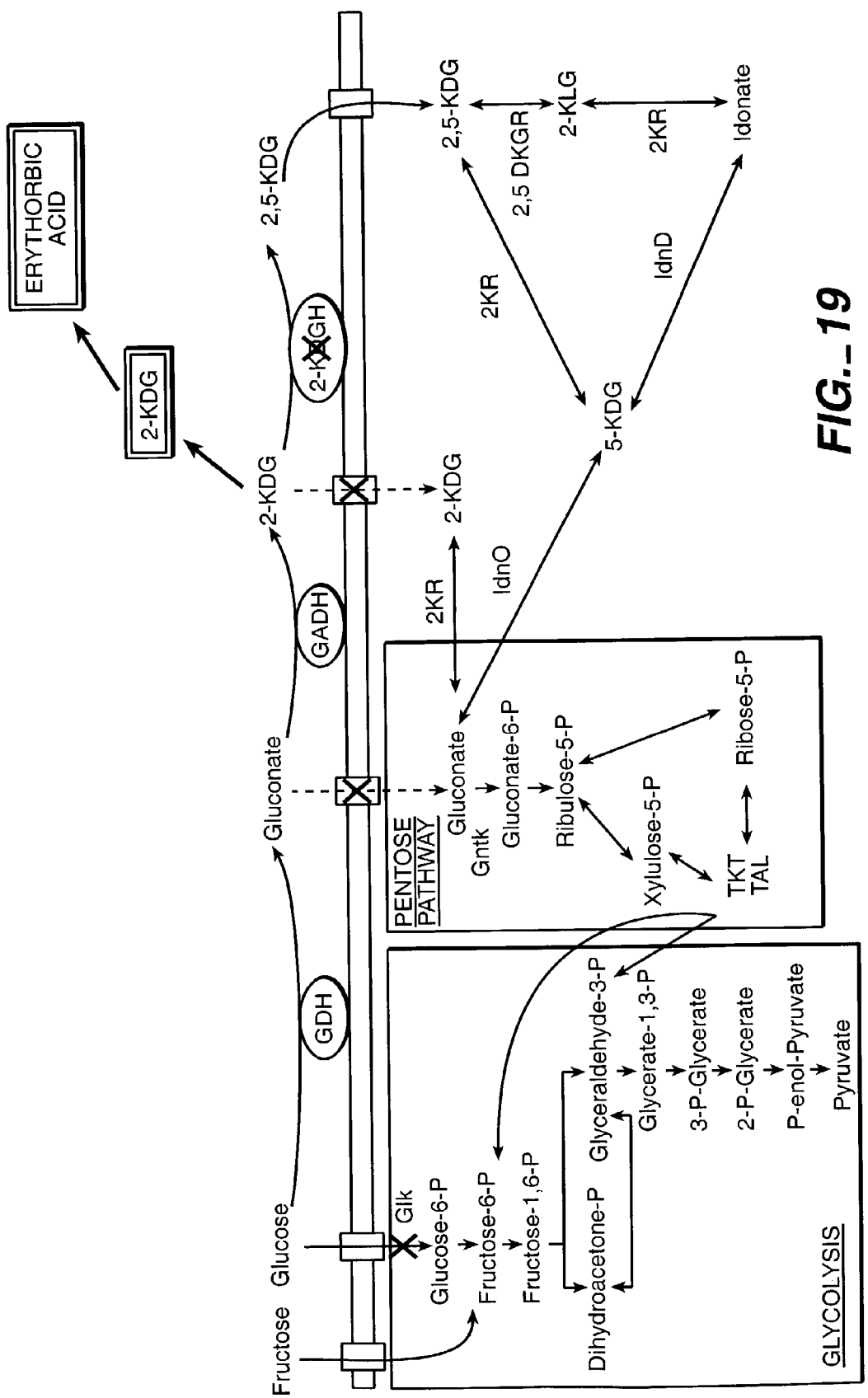
FIG._19

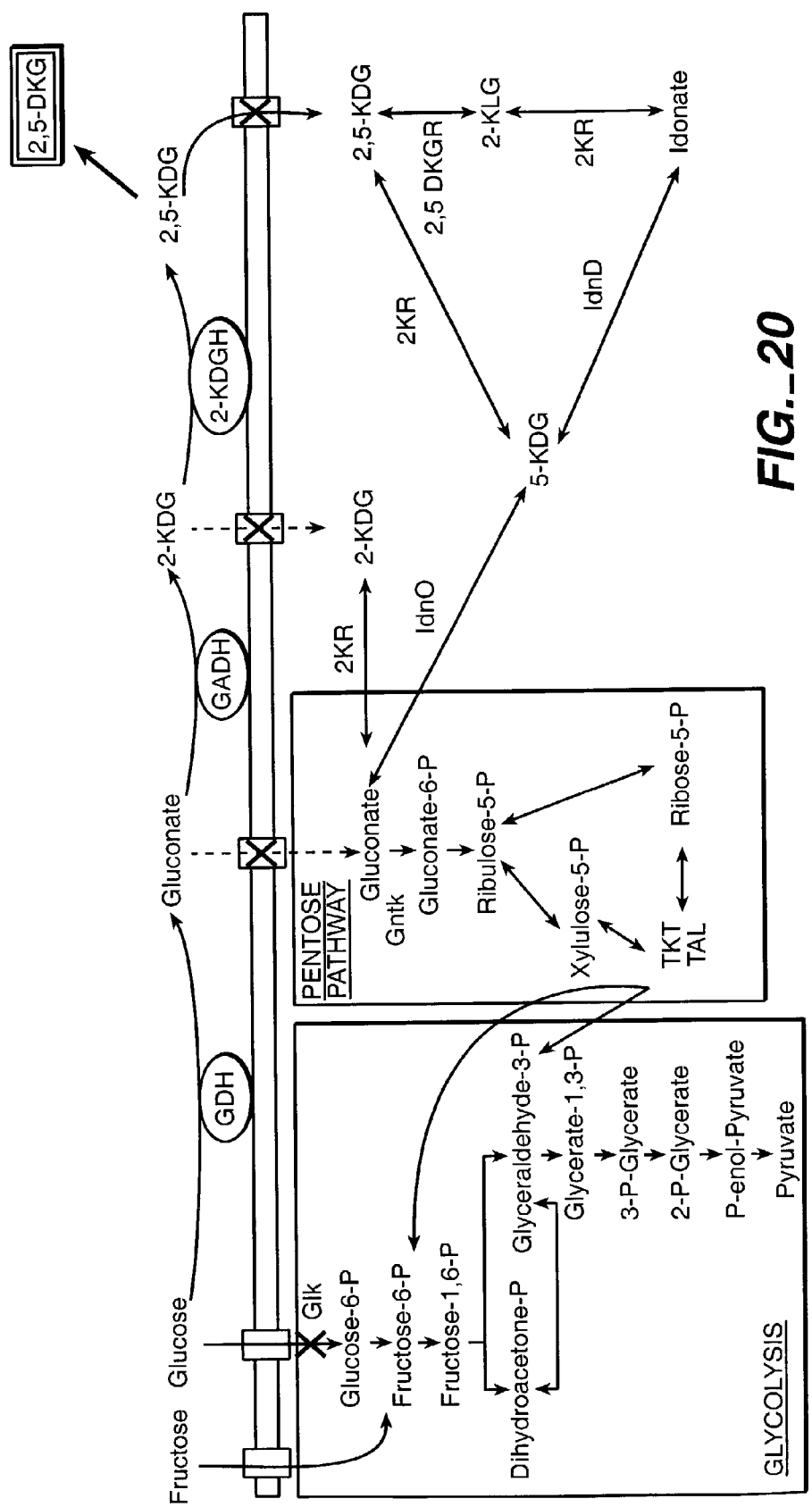
FIG._20

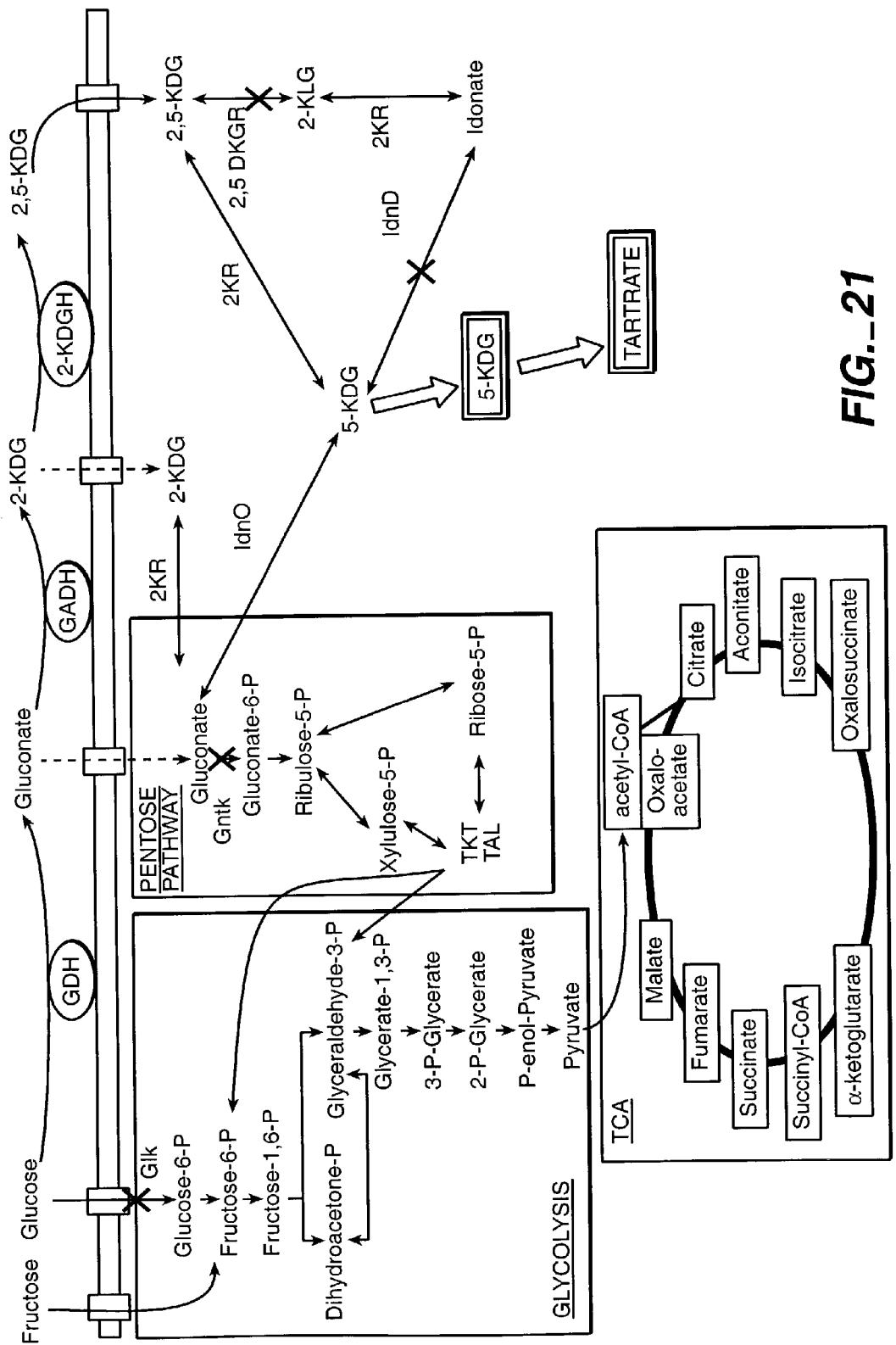
FIG._21

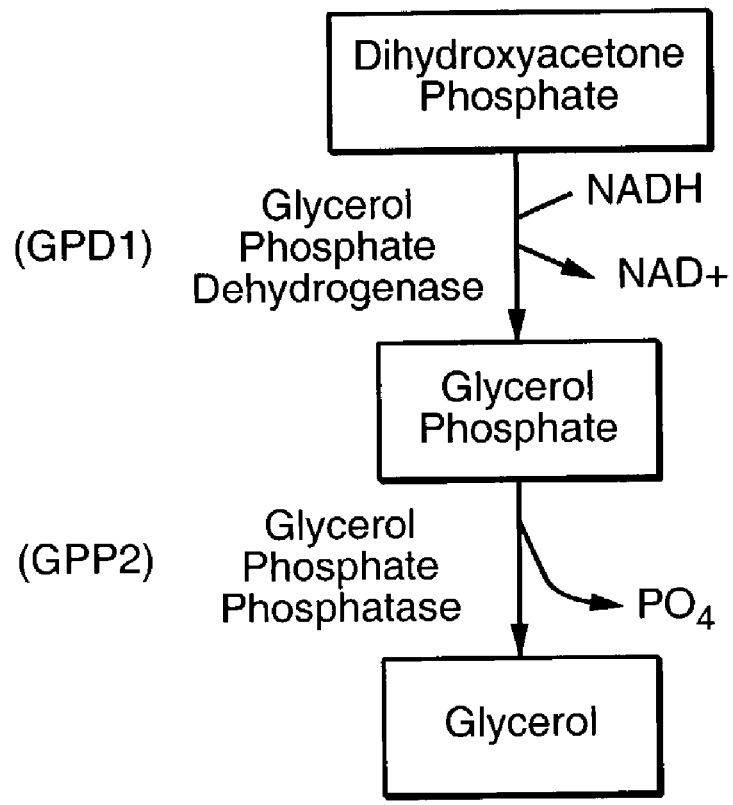
FIG._22
GlpK1
5' TGCAGTTTCAATGGGTGTTTA 3'
GlpK2
5' TGTCCGGCATGCAGGTCAGA 3'
FIG._23

ATG-ACTAACGCTGAAAACAAATACATTGTTGCACTGGACCAGGGAACCACCAGCTCACGA
GCGGTAGTACTGGATCACGATGCAAATATTATCGCGGTTTCACAACGTGAATTTACTCAG
CACTATCCTAAAACAGGCTGGGTTGAGCATGACCCGATGGATATCTGGGCAACCCAGAGT
TCAACTCTGGTAGAAGTACTGGCACACGCCGATATTCGTTCTGATCAGATTGCGGCGATT
GGTATTACTAACCAGCGTGAAACCACCATCGTCTGGGATAAGAAAACCGGCAAGCCTGTC
TATAACGCAATTGTCTGGCAGGACCCACGCACCGCTGACTACTGCTCAAAACTGAAAAAA
GAAGGTCTTGAAGAATATATTCAGAAGACGACCGGGCTTGTGATTAACCCTTACTTCTCC
GGAACCAAAATAAAATGGATTCTGGACAATGTGGAAGGTGCCCGGGATCGAGCCAAACGT
GGGGAACTGTTATTTGGTACCGTTGACACCTGGCTGGTCTGGAAAATGACTCAGGGTCGT
GTGCATGTTACCGACTTTACCAATGCTTCACGTACCATGATATTTGATATTCACAATCTG
AAGTGGGATGACCGTATGCTGGACATCCTTGATATTCCACGTGAAATGCTGCCAGAAGTT
AAAGCATCTTCTGAAGTTTACGGGCAGACAAACATCGGTGGTAAAGGCGGAACCCGTATT
CCGATCGCCGGGATCGCTGGTGATCAGCAGGCGGCTTTATACGGCCAGCTCTGTGTGCAA
CCAGGTATGGCGAAGAATACGTATGGTACCGGCTGCTTTATGTTAATGAATACCGGTACA
GAAGCAGTAGCTTCTACTCATGGCCTGCTGACAACAATTGCCTGCGGTCCACGGGGTGAA
GTTAACTATGCGCTGGAAGGTGCAGTCTTTATTGGCGGTGCTTCCATTCAATGGCTGCGT
GATGAGATGAAACTGTTCTCTGAAGCTTTAGACTCTGAATATTTCGCCACCAAAGTAAAA
GACTCTAACGGGGTTTATATGGTGCCGGCATTTACCGGTTTAGGCGCTCCGTACTGGGAC
CCATATGCCCGTGGAGCAATTTTTGGCCTGACCCGCGGAACCAATGCTAACCATATTATC
CGCGCTACTCTGGAATCTATTGCCTACCAGACTCGCGACGTGCTGGAAGCAATGCAGAAT
GATGCGAATACCCGTCTGCAGTCATTGCGGGTAGATGGTGGCGCTGTGGCGAATAATTTC
CTGATGCAATTCCAGTCCGATATTCTCGGAACACGGGTTGAGCGTCCGGAAGTTCGTGAA
GTCACCGCTCTTGGAGCTGCCTATCTGGCCGGGCTGGCAGTTGGATTCTGGAAAGATCTG
GATGAAGTCCGTTCGAAAGCGGTTATTGAGCGCGAGTTCCGCCCTTCAATCGAAACGACT
GAACGTAACTTCCGTTATGCCGGCTGGAAAAAGCTGTTTCCGCGCCCTGCGCTGGGAA
GATGAAAACGAACAA-TAA
```

FIG._24

MTNAENKYIVALDQGTTSSRAVVLDHDANIIAVSQREFTQHYPKTGWVEHDPMDIWATQ
SSTLVEVLAHADIRSDQIAAIGITNQRETTIVWDKKTGKPVYNAIVWQDPRTADYCSKL
KKEGLEEYIQKTTGLVINPYFSGTKIKWILDNVEGARDRAKRGELLFGTVDTWLVWKMT
QGRVHVTDFTNASRTMIFDIHNLKWDDRMLDILDIPREMLPEVKASSEVYGQTNIGGKG
GTRIPIAGIAGDQQAALYGQLCVQPGMAKNTYGTGCFMLMNTGTEAVASTHGLLTTIAC
GPRGEVNYALEGAVFIGGASIQWLRDEMKLFSEALDSEYFATKVKDSNGVYMVPAFTGL
GAPYWDPYARGAIFGLTRGTNANHIIRATLESIAYQTRDVLEAMQNDANTRLQSLRVDG
GAVANNFLMQFQSDILGTRVERPEVREVTALGAAYLAGLAVGFWKDLDEVRSKAVIERE
FRPSIETTERNFRYAGWKKAVSRALRWEDENEQ

METHODS FOR THE PRODUCTION OF PRODUCTS IN HOST CELLS

This application claim priority to provisional application Ser. No. 60/281,571, filed Apr. 4, 2001 and to provisional application Ser. No. 60/282,277, filed Apr. 5, 2001.

STATEMENT OF RIGHTS TO INVENTIONS MADE UNDER FEDERALLY SPONSORED RESEARCH

This invention was made with the United States Government support under Award No. 70 NANB 5H1138 awarded by the United States Department of Commerce. The Government has certain rights in this invention.

TECHNICAL FIELD

The present invention relates to engineering of metabolic pathways in host cells and provides methods and systems for the production of products in host cells. In particular, the present invention provides methods and systems for the production of ascorbic acid intermediates in host cells.

BACKGROUND ART

Numerous products of commercial interest, such as intermediates of L-ascorbic acid, have been produced biocatalytically in genetically engineered host cells. L-Ascorbic acid (vitamin C, ASA) finds use in the pharmaceutical and food industry as a vitamin and antioxidant. The synthesis of ASA has received considerable attention over many years due to its relatively large market volume and high value as a specialty chemical.

The Reichstein-Grussner method, a chemical synthesis route from glucose to ASA, was first disclosed in 1934 (Helv. Chim. Acta 17:311–328). Lazarus et al. (1989, "Vitamin C: Bioconversion via a Recombinant DNA Approach", Genetics and Molecular Biology of Industrial Microorganisms, American Society for Microbiology, Wash. D.C. Edited by C. L. Hershberger) disclose a bioconversion method for production of an intermediate of ASA, 2-keto-L-gulonic acid (2-KLG, KLG) which can be chemically converted to ASA. This bioconversion of carbon source to KLG involves a variety of intermediates, the enzymatic process being associated with co-factor dependent 2,5-DKG reductase activity (2,5-DKGR or DKGR).

Many bacterial species have been found to contain DKGR, particularly members of the Coryneform group, including the genera *Corynebacterium, Brevibacterium*, and *Arthrobacter*. DKGR obtained from *Corynebacterium* sp. strain SHS752001 is described in Grindley et al. (1988) Applied and Environmental Microbiology 54: 1770–1775. DKGR from *Erwinia herbicola* is disclosed in U.S. Pat. No. 5,008,193 to Anderson et al. Other reductases are disclosed in U.S. Pat. Nos. 5,795,761; 5,376,544; 5,583,025; 4,757,012; 4,758,514; 5,004,690; and 5,032,514.

Host cells having mutations in enzymes involved in glycolysis have been described. Yeast having mutations in glucokinase are described in Harrod, et al. (1997) J. Ind. Microbiol. Biotechnol. 18:379–383; Wedlock, et al. (1989) J. Gen. Microbiol. 135: 2013–2018; and Walsh et al. (1983) J. Bacteriol. 154:1002–1004. Bacteria deficient in glucokinase have been described. *Pediococcus* sp. deficient in glucokinase is described in Japanese patent publication JP 4267860. *Bacillus sphaericus* lacking glucokinase is described in Russell et al. (1989) Appl. Environ. Microbiol. 55: 294–297. *Penicillium chrysogenum* deficient in glucokinase is described in Barredo et al. (1988) Antimicrob. Agents-Chemother 32: 1061–1067. A glucokinase-deficient mutant of *Zymomonas mobilis* is described in DiMarco et al. (1985) Appl. Environ. Microbiol. 49:151–157.

Bacteria which ferment glucose through the Embden-Meyerhof pathway, such as members of *Enterobacteriacea* and *Vibrionaceae*, are described in Bouvet, et al. (1989) International Journal of Systematic Bacteriology, p. 61–67. Pathways for metabolism of ketoaldonic acids in *Erwinia* sp. are described in Truesdell, et al, (1991) Journal of Bacteriology, pp 6651–6656.

However, most of the current methodologies utilized to produce compounds over-express the products. There are still problems remaining concerning the diversion of substrates used to produce the desired end-product by the cell for metabolic (catabolic) purposes, reducing the efficiency and overall production of thereof. Thus, there remains a need for improved methods for the production of products through pathways which are coupled to the metabolic pathways of host cells. The present invention addresses that need.

All publications cited herein are hereby incorporated by reference in their entirety.

SUMMARY OF THE INVENTION

The present invention provides methods to produce ascorbic acid intermediates comprising host cells genetically engineered to reduce carbon substrate diverted to metabolic pathways, thus increasing the productivity of the host cell.

In one embodiment, the present invention provides a method of enhancing the production of an ascorbic acid intermediate from a carbon source comprising,
  a) obtaining an altered bacterial strain which comprises inactivating a chromosomal gene in a bacterial host strain,
  b) culturing said altered bacterial host strain under suitable conditions, and
  c) allowing the production of an ascorbic acid intermediate from the carbon source, wherein the production of said ascorbic acid intermediate is enhanced compared to the production of the ascorbic acid intermediate in the unaltered bacterial host strain.

The ascorbic acid intermediate can be selected from the group consisting of gluconate, 2-keto-D-gluconate, 2,5-diketo-D-gluconate, 2-keto-L-gulonic acid, L-iodonic acid, erthorbic acid, and tartrate. In a particular embodiment, the intermediate is 2,5-diketo-D-gluconate. The altered bacterial strain can be obtained by the inactivation of a glk chromosomal gene. The altered bacterial strain can also be obtained by the inactivation of a gntk chromosomal gene. The altered bacterial strain can also be obtained by the inactivation of a glk and a gntk chromosomal gene. The bacterial strain can be *Pantoea*, more specifically, *Pantoea citrea*.

In one embodiment, such host cells have a modification in a polynucleotide encoding an enzymatic activity that phosphorylates D-glucose at its 6th carbon and/or a modification in a polynucleotide encoding an enzymatic activity that phosphorylates D-gluconate at its 6th carbon. Such host cells when cultured in the presence of a carbon source demonstrated increased yield of product as measured directly and/or indirectly. In some embodiments of the invention, the methods comprise host cells having a modification in a polynucleotide encoding an enzymatic activity that phosphorylates D-glucose at its 6th carbon and a modification in a polynucleotide encoding an enzymatic activity that phosphorylates D-gluconate at its 6th carbon.

Accordingly, in one aspect, the invention provides a process for producing an ascorbic acid intermediate in a recombinant host cell comprising, culturing a host cell capable of producing said ascorbic acid intermediate in the presence of glucose, or a carbon source that can be converted to glucose by the host cell, under conditions suitable for the production of said ascorbic acid intermediate wherein said host cell is modified to reduce the glucose diverted to the catabolic pathway of the organism. The modification, can comprise at least one polynucleotide encoding an enzymatic activity that diverts such carbon substrate to such catabolic pathway is inactivated or deleted such that the level of said enzymatic activity is correspondingly affected during said culturing.

In some embodiments of the present invention, the host cell further comprises at least one polynucleotide encoding an enzymatic activity that phosphorylates D-gluconate at its 6th carbon wherein said polynucleotide has been modified such that the level of said enzymatic activity is modified during said culturing to inactivate or reduce the amount of substrate transported across the cell membrane and/or phosphorylated for utilization within the cell's catabolic pathways. In some embodiments, the process comprises the step of recovering said product and in other embodiments, the process comprises the step of converting said product to a second product.

In some embodiments, the level of endogenous enzymatic activity is regulated during culturing, such as by transcriptional or translational regulatory elements. Accordingly, in some embodiments, the polynucleotide encoding an enzymatic activity that phosphorylates D-glucose for transport across the cell membrane is operably linked to a regulatable promoter. In other embodiments, the polynucleotide encoding an enzymatic activity that phosphorylates D-gluconate at its 6th carbon is operably linked to a regulatable promoter. In other embodiments, the endogenous enzymatic activity is inactivated, such as by mutation in or deletion of part or all of a polynucleotide encoding the enzymatic activity.

The present invention encompasses production of ascorbic acid intermediates including gluconate, 2-keto-D-gluconate (2-KDG or KDG); 2,5-diketo-D-gluconate (2,5DKG or DKG); 2-keto-L-gulonic acid (2KLG, or KLG); or L-idonic acid (IA). In some embodiments, the ascorbic acid intermediate is KLG and the KLG is converted to ascorbic acid. In other embodiments, the ascorbic acid intermediate is KDG and the KDG is converted to erythorbate.

The present invention provides recombinant host cells capable of producing an ASA intermediate, wherein said host cell comprises a polynucleotide encoding an enzymatic activity that phosphorylates D-glucose at its 6th carbon, wherein said polynucleotide is modified. The invention also provides recombinant host cells further comprising a polynucleotide encoding an enzymatic activity that phosphorylates D-gluconate at its 6th carbon, wherein said polynucleotide is modified.

In some embodiments, the host cell is a Gram positive microorganism and in other embodiments, the host cell is a Gram negative microorganism. In some embodiments, the Gram negative host cell is an *Enterobacteriaceae* host cell including *Erwinia, Enterobacter, Gluconobacter, Acetobacter, Corynebacteria, Escherichia, Salmonella, Klebsiella* or *Pantoea*.

In other embodiments, the host cell can be any bacteria that naturally or after proper genetic modifications, is able to utilize one carbon source to maintain certain cell functions, for example, but not limited to, the generation of reducing power in the form of NAD, $FADH_2$ or NADPH, while another carbon source is converted into one or more product(s) of commercial interest.

In some embodiments, the enzymatic activity that phosphorylates D-glucose at its $6^{th}$ carbon includes glucokinase, hexokinase, the phosphotransferase system (PTS) or any other enzyme(s) not necessarily classified under the 3 previous groups, but capable of such a function. For example, it is possible that an enzyme maybe classified as a fructokinase because its preferred substrate is fructose, can phosphorylate D-glucose at a measurable rate. It is not uncommon that enzymes will act on other similar substrates, especially at high levels of substrates.

In other embodiments, the enzymatic activity that phosphorylates D-gluconate at its $6^{th}$ carbon includes gluconokinase, deoxygluconokinase, hexokinase, the phosphotransferase system (PTS) or any other enzyme(s) not necessarily classified under the 4 previous groups, but capable of such a function. For example, It is possible that an enzyme maybe classified as a deoxyglukono-kinase because its preferred substrate is deoxygluconate, can phosphorylate D-gluconate at a measurable rate. It is not uncommon that enzymes will act on other similar substrates, especially at high levels of substrates.

The present invention also provides methods for producing host cells having modified levels of enzymatic activities. The present invention also provides novel nucleic acid and amino acid sequences for enzymatic activity that phosphorylates D-glucose at its 6th carbon and enzymatic activity that phosphorylates D-gluconate at its 6th carbon.

The present invention also provides methods for producing host cells capable to produce different biomolecules of industrial importance derived from glucose and/or fructose.

The present invention also provides host cells having modified levels of enzymatic activities. The present invention also provides novel nucleic acid and amino acid sequences for enzymatic activity that phosphorylates D-glucose at its 6th carbon and enzymatic activity that phosphorylates D-gluconate at its 6th carbon.

The present invention also provides host cells capable to produce different biomolecules of industrial importance derived from glucose and/or fructose.

BRIEF DESCRIPTION OF THE DRAWINGS

FIG. 1 provides a schematic representation of some of the metabolic routes involved in Glucose assimilation in *Pantoea citrea*. The enzymatic steps affected by the genetic modifications described in the present invention, are indicated by an X. Boxes labeled with a T represent putative transporters.

FIG. 2. Some possible catabolic routes that can be used to channel glucose into cellular metabolism. The arrows represent at least one enzymatic step.

FIG. 3. depicts products that can be obtained from indicated commercial routes. The majority of the carbon used to synthesize the compounds listed on the left side, can be obtained from the catabolic pathway or TCA cycle. On the contrary, the compounds on the right, derive most of its carbon from the pentose pathway and/or from the oxidation of glucose into keto-acids.

FIG. 4 depicts a nucleic acid (SEQ ID NO:1) sequence for a *Pantoea citrea* glucokinase (glk).

FIG. 5 depicts an amino acid (SEQ ID NO:2) sequence for a *Pantoea citrea* glucokinase (Glk).

FIG. 6 depicts a nucleic acid (SEQ ID NO:3) sequence for a *Pantoea citrea* gluconokinase (gntk)

FIG. 7 depicts an amino acid (SEQ ID NO:4) sequence for a *Pantoea citrea* gluconokinase (Gntk).

FIG. 8 depicts amino acid (SEQ ID NO: 5–10) for the genes glk 30, glk 31, gnt 1, gnt 2, pcgnt 3 and pcgnt 4.

FIG. 9 depicts D-glucose, D-gluconate and some of their derivatives. The standard numbering of the carbons on glucose is indicated by the numbers 1 and 6. 2-KDG=2-keto-D-gluconate; 2,5-DKG=2,5-diketogluconate; 2KLG=2-keto-L-gulonate.

FIG. 10 depicts general strategy used to interrupt the gluconate kinase gene from *P. citrea*.

FIG. 11 depicts the oxidative pathway for the production of ascorbic acid. E1 stands for glucose dehydrogenase; E2 stands for gluconic acid dehydrogenase; E3 stands for 2-keto-Dgluconic acid dehydrogenase; and E4 stands for 2,5-diketo-D-gluconic acid reductase.

FIG. 12 depicts the net reactions during the fermentation of host cells capable of producing ascorbic acid intermediates.

FIG. 13 depicts carbon evolution rate (CER) and oxygen uptake rate (OUR) of a fermentation of a wild-type organism after exposure to glucose.

FIG. 14 depicts the CER and OUR of a fermentation with a single delete (glucokinase).

FIG. 15 depicts the CER and OUR of a fermentation with a single delete (gluconokinase).

FIG. 16 depicts the CER and OUR of a fermentaion with a host cell having both glucokinase and gluconokinase deleted.

FIG. 17 is a schematic illustrating the interrelationships of various metabolic pathways (including the glycolytic pathway, TCA cycle, and pentose pathway) and the oxidative pathways. Glk=glucokinase; Gntk=gluconokinase; IdnO=Idonate reductase; IdnD=Idonate dehydrogenase; TKT=transketolase; TAL=transaldolase, 2KR=2-keto reductase; 2,5DKGR=2,5-diketogluconate reductase.

FIG. 19 is a schematic illustrating the interrelationships of various central metabolic pathways and the modifications which would increase the production of erythorbic acid. The X indicate the enzymatic pathways that would be modified to effect the desired increase in erythorbic acid production.

FIG. 20 is a schematic illustrating the interrelationships of various central metabolic pathways and the modifications which would increase the production of ribose. The X indicate the enzymatic or transport pathways that would be modified to effect the desired increase in 2,5-diketogluconate production.

FIG. 21 is a schematic illustrating the interrelationships of various central metabolic pathways and the modifications which would increase the production of tartrate. The X indicate the enzymatic steps that would be modified to effect the desired increase in ribose production. IdnO=5-keto-D-gluconate 5-reductase; IdnD=I-Idonate 5-dehydrogenase.

FIG. 22 is a schematic illustrating the pathway of dihydroxyacetone phosphate (DHAP) being converted to glycerol.

FIG. 23 depicts the DNA sequence of primers, glpk1 (SEQ ID NO: 11) and glpk2 (SEQ ID NO: 12) used to amplify by PCR the 2.9 kb DNA fragment that contains the glpK gene as described in Example 7.

FIG. 24 describes the DNA sequence (SEQ ID NO: 13) of the structural gene of the glycerol kinase from *P. citrea* as described in Example 7. The sequence of the HpaI site used to interrupt the gene is underlined.

FIG. 25 depicts the protein sequence (SEQ ID NO: 14) of the glycerol kinase from *P. citrea* as described in Example 7.

DETAILED DESCRIPTION

Figure 18:
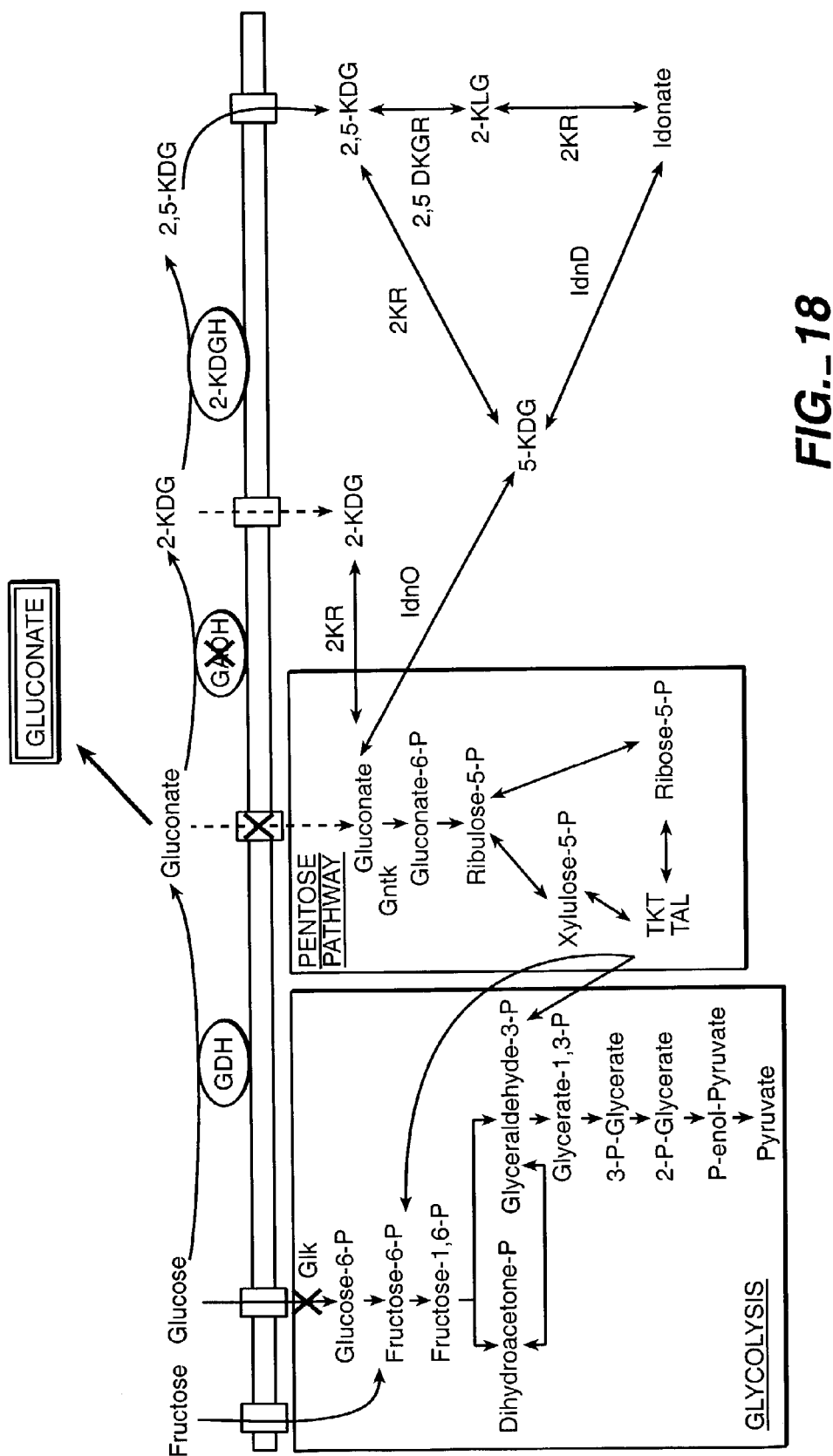
FIG. 18 is a schematic illustrating the interrelationships of various central metabolic pathways and the modifications which would increase the production of gluconate. The X indicate the enzymatic pathways that would be modified to effect the desired increase in gluconate production.

The invention provides methods and host cells for the production of ascorbic acid intermediates. Recombinant host cells have been constructed which produce ascorbic acid intermediates and which are genetically engineered to reduce the carbon substrate diverted to catabolic pathways. In one embodiment, the recombinant host cells produce modified levels of enzymatic activity that transports into the cell for use in the catabolic pathways, e.g., those that phosphorylate D-glucose at its 6th carbon and/or enzymatic activity that phosphorylates D-gluconate at its 6th carbon. When these recombinant cells are cultured in the presence of glucose or a carbon source which can be converted to glucose by the host cell, intracellular metabolism of the glucose and/or gluconate is reduced.

In some embodiments, the host cell is a *Pantoea citrea* cell which has been genetically engineered to produce a product, such as an ascorbic acid ("ASA") intermediate. In these embodiments, a particular advantage provided by the invention is the ability to make use of fermentation processes for the production of the ASA intermediate.

Another advantage provided by the invention is the uncoupling of the extracellular oxidation of a substrate from the metabolic pathways that use those oxidation products.

Another advantage provided by the invention is the increased efficiency in the production of ascorbic acid intermediates as compared to wild-type bioconversion as measured directly by increased production of the desired product or indirectly as measured by oxygen consumption or $CO_2$ off gas ($CO_2$ production).

A further advantage provided by the invention is the ability of the host cell to utilize two different carbon sources simultaneously for the production of ascorbic acid intermediates.

General Techniques

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, Molecular Cloning: A Laboratory Manual, second edition (Sambrook et al., 1989); Current Protocols in Molecular Biology (F. M. Ausubel et al., eds., 1987 and annual updates); Oligonucleotide Synthesis (M. J. Gait, ed., 1984); and PCR: The Polymerase Chain Reaction, (Mullis et al., eds., 1994). Manual of Industrial Microbiology and Biotechnology, Second Edition (A. L. Demain, et al., eds. 1999)

Definitions

As used herein, "oxidative pathway of a host cell" means that the host cell comprises at least one oxidative enzyme that oxidizes a carbon source, such as, D-glucose and/or its metabolites. A "membrane" or "membrane bound" glucose oxidative pathway in a host cells refers to a host cell that oxidizes a carbon source such as, D-glucose and/or its metabolites, via at least one membrane bound oxidative enzymatic activity. In some embodiments, an oxidative pathway in a host cell comprises one enzymatic activity. In other embodiments, an oxidative pathway in a host cell comprises two or more enzymatic activities.

As used herein, "catabolic pathway of a host cell" means that the host cell comprises at least one enzymatic activity that generates ATP or NADPH, for example, by phosphorylating a carbon source, such as D-glucose and/or its metabolites. An "intracellular" catabolic pathway in a host cell means that the host cell comprises at least one such enzymatic activity in the host cell cytosol. In some embodiments, a catabolic pathway in a host cell comprises one enzymatic activity. In other embodiments, a catabolic pathway in a host cell comprises two or more enzymatic activities. Catabolic pathways include, but are not limited to glycolysis, the pentose pathway and the TCA pathway (see FIG. 17).

As used herein, the phrase "enzymatic transport system" refers to an enzymatic activity that consumes energy (ATP) and transports the carbon substrate across the cell membrane, usually by adding a phosphate to the 6th carbon of D-glucose and includes the enzymatic activities glucokinase (E.C.-2.7.1.2) and phosphotransferase system (PTS) (E.C.-2.7.1.69).

As used herein, the phrase "enzymatic activity which phosphorylates D-gluconate at its 6th carbon" refers to an enzymatic activity that phosphorylates D-gluconate at its 6th carbon and includes the enzymatic activity gluconokinase (E.C.-2.7.1.12).

As used herein, the phrase "enzymatic activity which phosphorylates D-glucose at its 6th carbon" refers to an enzymatic activity that adds a phosphate to the 6th carbon of D-glucose and includes the enzymatic activities glucokinase (E.C.-2.7.1.2); and phosphotransferase system (PTS) (E.C.-2.7.1.69).

As used herein, the phrase "enzymatic activity which phosphorylates D-gluconate at its 6th carbon" refers to an enzymatic activity that phosphorylates D-gluconate at its 6th carbon and includes the enzymatic activity gluconokinase (E.C.-2.7.1.12).

As used herein, "modifying" the levels of an enzymatic activity produced by a host cell or "modified levels" of an enzymatic activity of a host cell refers to controlling the levels of enzymatic activity produced during culturing, such that the levels are increased or decreased as desired. The desired change in the levels of enzymatic activity may be genetically engineered to take place in one or both enzymatic activities either simultaneously or sequentially, in any order. In order to control the levels of enzymatic activity, the host cell is genetically engineering such that nucleic acid encoding the enzymatic activity is transcriptionally or translationally controlled.

As used herein, the term "modified" when referring to nucleic acid or polynucleotide means that the nucleic acid has been altered in some way as compared to wild type nucleic acid, such as by mutation in; deletion of part or all of the nucleic acid; or by being operably linked to a transcriptional control region. As used herein the term "mutation" when referring to a nucleic acid refers to any alteration in a nucleic acid such that the product of that nucleic acid is partially or totally inactivated or eliminated. Examples of mutations include but are not limited to point mutations, frame shift mutations and deletions of part or all of a gene encoding an enzymatic activity, such as an enzymatic activity that transports the substrate across the cell membrane, e.g., phosphorylates D-glucose at its 6th carbon or an enzymatic activity that phosphorylates D-gluconate at its 6th carbon.

An "altered bacterial strain" according to the invention is a genetically engineered bacterial microorganism having an enhanced level of production over the level of production of the same end-product in a corresponding unaltered bacterial host strain grown under essentially the same growth conditions. An "unaltered bacterial strain" or host is a bacterial microorganism wherein the coding sequence of the diverting enzymatic pathway is not inactivated and remains enzymatically active. The enhanced level of production results from the inactivation of one or more chromosomal genes. In a first embodiment the enhanced level of expression results from the deletion of one or more chromosomal genes. In a second embodiment the enhanced level of expression results from the insertional inactivation of one or more chromosomal genes. Preferably the inactivated genes are selected from those encoding the enzymes whose inactivity is desired as described elsewhere in this application. For example, in one embodiment one or more chromosomal genes selected from the group consisting of glk, and gntk.

In certain embodiments, the altered *Bacillus* strain may embody two inactivated genes, three inactivated genes, four inactivated genes, five inactivated genes, six inactivated genes or more. The inactivated genes may be contiguous to one another or may be located in separate regions of the *Bacillus* chromosome. An inactivated chromosomal gene may have a necessary function under certain conditions, but the gene is not necessary for *Bacillus* strain viability under laboratory conditions. Preferred laboratory conditions include but are not limited to conditions such as growth in a fermentator, in a shake plate, in plate media or the like.

As used herein, the term "inactivation" or "inactivating" when referring to an enzymatic activity means that the activity has been eliminated by any means including a mutation in or deletion of part or all of the nucleic acid encoding the enzymatic activity. The term "inactivation" or "inactivating" includes any method that prevents the functional expression of one or more of the desired chromosomal genes, wherein the gene or gene product is unable to exert its known function. The desired chromosomal genes will depend upon the enzymatic activity that is intended to be inactivated. For example the inactivation of glucokinase and/or gluconokinase activity can be effected by inactivating the glk and/or gntk chromosomal genes. Inactivation may include such methods as deletions, mutations, interruptions or insertions in the nucleic acid gene sequence. In one embodiment, the expression product of an inactivated gene may be a truncated protein as long as the protein has a change in its biological activity. The change in biological activity could be an altered activity, but preferably is loss of biological activity. In an altered bacterial strain according to the invention, the inactivation of the one or more genes will preferably be a stable and non-reverting inactivation.

In a preferred embodiment, preferably a gene is deleted by homologous recombination. For example, as shown in FIG. 9, when glk is the gene to be deleted, a chloramphenicol resistance gene is cloned into a unique restriction site found in the glucokinase gene. The $Cm^R$ gene is inserted into the structural coding region of the gene at the Pst I site. Modification is then transferred to the chromosome of a *P. citrea* glkA- by homologous recombination using a non-replication R6K vector. The $Cm^R$ gene is subsequently removed from the glk coding region leaving an interrupting spacer in the coding region, inactivating the coding region. In another embodiment, the $Cm^R$ gene is inserted into the coding region in exchange for portions of the coding region. Subsequent removal of the $Cm^R$ gene without concomitant reinsertion of the exchanged out portion of the coding region results in an effective deletion of a portion of the coding region, inactivating such region.

A deletion of a gene as used herein may include deletion of the entire coding sequence, deletion of part of the coding sequence, or deletion of the coding sequence including flanking regions. The deletion may be partial as long as the sequences left in the chromosome are too short for biological activity of the gene. The flanking regions of the coding sequence may include from about 1 bp to about 500 bp at the 5' and 3' ends. The flanking region may be larger than 500 bp but will preferably not include other genes in the region which may be inactivated or deleted according to the invention. The end result is that the deleted gene is effectively non-functional.

In another preferred embodiment, inactivation is by insertion. For example when glk is the gene to be inactivated, a DNA construct will comprise an incoming sequence having the glk gene interrupted by a selective marker. The selective marker will be flanked on each side by sections of the glk coding sequence. The DNA construct aligns with essentially identical sequences of the glk gene in the host chromosome and in a double crossover event the glk gene is inactivated by the insertion of the selective marker.

In another embodiment, activation is by insertion in a single crossover event with a plasmid as the vector. For example, a glk chromosomal gene is aligned with a plasmid comprising the gene or part of the gene coding sequence and a selective marker. The selective marker may be located within the gene coding sequence or on a part of the plasmid separate from the gene. The vector is integrated into the Bacillus chromosome, and the gene is inactivated by the insertion of the vector in the coding sequence.

Inactivation may also occur by a mutation of the gene. Methods of mutating genes are well known in the art and include but are not limited to chemical mutagenesis, site-directed mutation, generation of random mutations, and gapped-duplex approaches. (U.S. Pat. No. 4,760,025; Moring et al., *Biotech.* 2:646 (1984); and Kramer et al., *Nucleic Acids Res.* 12:9441 (1984)).

Inactivation may also occur by applying the above described inactivation methods to the respective promoter regions of the desired genomic region. "Under transcriptional control" or "transcriptionally controlled" are terms well understood in the art that indicate that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

As used herein, the term "regulatable promoter" refers to a promoter element which activity or function can be modulated. This modulation can be accomplished in many different ways, most commonly by the interaction of protein(s) that interfere or increase the ability of the RNA polymerase enzyme to initiate transcription.

"Under translational control" is a term well understood in the art that indicates a regulatory process that occurs after the messenger RNA has been formed.

As used herein, the term "batch" describes a batch cell culture to which substrate, in either solid or concentrated liquid form, is added initially at the start of the run. A batch culture is initiated by inoculating cells to the medium, but, in contrast to a fed-batch culture, there is no subsequent inflow of nutrients, such as by way of a concentrated nutrient feed. In contrast to a continuous culture, in a batch cell culture, there is no systematic addition or systematic removal of culture fluid or cells from a culture. There is no ability to subsequently add various analytes to the culture medium, since the concentrations of nutrients and metabolites in culture medium are dependent upon the initial concentrations within the batch and the subsequent alteration of the composition of the nutrient feed due to the act of fermentation.

As used herein, the term "fed-batch" describes a batch cell culture to which substrate, in either solid or concentrated liquid form, is added either periodically or continuously during the run. Just as in a batch culture, a fed-batch culture is initiated by inoculating cells to the medium, but, in contrast to a batch culture, there is a subsequent inflow of nutrients, such as by way of a concentrated nutrient feed. In contrast to a continuous culture there is no systematic removal of culture fluid or cells from a fed-batch culture is advantageous in applications that involve monitoring and manipulating the levels of various analytes in the culture medium, since the concentrations of nutrients and metabolites in culture medium can be readily controlled or affected by altering the composition of the nutrient feed. The nutrient feed delivered to a fed-batch culture is typically a concentrated nutrient solution containing an energy source, e.g., carbohydrates; optionally, the concentrated nutrient solution delivered to a fed-batch culture can contain amino acids, lipid precursors and/or salts. In a fed-batch culture, this nutrient feed is typically rather concentrated to minimize the increase in culture volume while supplying sufficient nutrients for continued cell growth.

The term "continuous cell culture" or, simply, "continuous culture" is used herein to describe a culture characterized by both a continuous inflow of a liquid nutrient feed and a continuous liquid outflow. The nutrient feed may, but need not, be a concentrated nutrient feed. Continuously supplying a nutrient solution at about the same rate that cells are washed out of the reactor by spent medium allows maintenance of a culture in a condition of stable multiplication and growth. In a type of bioreactor known as a chemostat, the cell culture is continuously fed fresh nutrient medium, and spent medium, cells and excreted cell product are continuously drawn off. Alternatively, a continuous culture may constitute a "perfusion culture," in which case the liquid outflow contains culture medium that is substantially free of cells, or substantially lower cell concentration than that in the bioreactor. In a perfusion culture, cells can be retained by, for example, filtration, centrifugation, or sedimentation.

"Culturing" as used herein refers to fermentative bioconversion of a carbon substrate to the desired end-product within a reactor vessel.

Bioconversion as used herein refers to the use of contacting a microorganism with the carbon substrate to convert the carbon substrate to the desired end-product.

As used herein, "Oxygen Uptake Rate or "OUR" refers to the determination of the specific consumption of oxygen within the reactor vessel. Oxygen consumption can be determined using various on-line measurements. In one example, the OUR (mmol/(liter*hour)) is determined by the following formula:

((Airflow (standing liters per minute)/Fermentation weight (weight of the fermentation broth in kilograms)) ×supply $O_2$×broth density×(a constant to correct for airflow calibration at 21.1 C instead of standard 20.0 C)) minus ([airflow/ fermentation weight]×[offgas $O_2$/offgas $N_2$] ×supply $N_2$ ×broth density ×constant).

As used herein, "carbon evolution rate or "CER" refers to the determination of how much $CO_2$ is produced within the reactor vessel during fermentation. Usually, since no $CO_2$ is initially or subsequently provided to the reaction vessel, any $CO_2$ is assumed to be produced by the fermentation process occurring within the reaction vessel. "Off-gas $CO_2$" refers to the amount of $CO_2$ measured within the reactor vessel, usually by mass spectroscopic methods known in the art.

As used herein, "yield" refers to the amount of product/ the amount of substrate. The yield can be expressed as a weight % (product gm/substrate gm) or as moles of product/ moles of substrate. For example, the amount of the substrate, e.g., glucose can be determined by the feed rate and the concentration of the added glucose. The amount of products present can be determined by various spectrophotometric or analytic methodologies. One such methodology is high performance liquid chromatography (HPLC). An increased yield refers to an increased yield as compared to the yield of a conversion using the wild-type organism, for example an increase of 10%, 20% or 30% over the yield of the wild-type.

The phrase "productive enzyme" as used herein refers to an enzyme or enzyme system which can catalyze conversion of a substrate to a desired product. Productive enzymes include, but are not limited to oxidative enzymes and reducing enzymes.

The phrase "oxidative enzyme" as used herein refers to an enzyme or enzyme system which can catalyze conversion of a substrate of a given oxidation state to a product of a higher oxidation state than substrate. The phrase "reducing enzyme" refers to an enzyme or enzyme system which can catalyze conversion of a substrate of a given oxidation state to a product of a lower oxidation state than substrate. In one illustrative example disclosed herein, oxidative enzymes associated with the biocatalysis of D-glucose or its metabolites in a *Pantoea* cell which has been engineered to produce ASA intermediates, include among others D-glucose dehydrogenase, D-gluconate dehydrogenase and 2-keto-D-gluconate dehydrogenase. In another illustrative embodiment disclosed herein, reducing enzymes associated with the biocatalysis of D-glucose or its metabolites in a *Pantoea* cell which has been engineered to produce ASA intermediates, as described herein, include among others 2,5-diketo-D-gluconate reductase, 2-keto reductase and 5-keto reductase. Such enzymes include those produced naturally by the host strain or those introduced via recombinant means.

As used herein, the term "carbon source" encompasses suitable carbon sources ordinarily used by microorganisms, such as 6 carbon sugars, including but not limited to glucose, gulose, sorbose, fructose, idose, galactose and mannose all in either D or L form, or a combination of 6 carbon sugars, such as glucose and fructose, and/or 6 carbon sugar acids including but not limited to 2-keto-L-gulonic acid, idonic acid, gluconic acid, 6-phosphogluconate, 2-keto-D-gluconic acid, 5-keto-D-gluconic acid, 2-ketogluconatephosphate, 2,5-diketo-L-gulonic acid, 2,3-L-diketogulonic acid, dehydroascorbic acid, erythrorbic acid and D-mannonic acid or the enzymatic derivatives of such.

The following abbreviations apply as used herein to D-glucose or glucose (G); D-gluconate or gluconate (GA); 2-keto-D-gluconate (2KDG); 2,5-diketo-D-gluconate (2,5DKG or DKG); 2-keto-L-gulonic acid (2KLG, or KLG); L-idonic acid (IA); erythorbic acid (EA); ascorbic acid (ASA); glucose dehydrogenase (GDH); gluconic acid dehydrogenase (GADH); 2,5-diketo-D-gluconate reductase (DKGR); 2-keto-D-gluconate reductase (KDGDH); D-ribose (R); 2-keto reductase (2KR or KR); and 5-keto reductase (5KR or KR).

"Allowing the production of an ascorbic acid intermediate from the carbon source, wherein the production of said ascorbic acid intermediate is enhanced compared to the production of the ascorbic acid intermediate in the unaltered bacterial host strain" means contacting the substrate, e.g. carbon source, with the altered bacterial strain to produce the desired end-product. The inventors discovered that by altering certain enzymatic activities by inactivating genomic expression, the microorganism demonstrated enhanced end-product production.

"Desired end-product" as used herein refers to the desired compound to which the carbon substrate is bioconverted into. The desired end-product may be the actual compound sought or an intermediate along another pathway. Exemplary desired end-products are listed on the right side of FIG. 3.

As used herein, the term bacteria refers to any group of microscopic organisms that are prokaryotic, i.e., that lack a membrane-bound nucleus and organelles. All bacteria are surrounded by a lipid membrane that regulates the flow of materials in and out of the cell. A rigid cell wall completely surrounds the bacterium and lies outside the membrane. There are many different types of bacteria, some of which include, and are not limited to those strains within the families of Enterobacteriaceae, Bacillus, Streptomyces, Pseudomonas, and Erwinia.

As used herein, the family "Enterobacteriaceae" refers to bacterial strains having the general characteristics of being Gram negative and being facultatively anaerobic, including the genus contained within *Escherichia coli, Shigella, Edwardsiella; Salmonelle; Citrobacter, Klebsiella, Enterobacter, Serratia, Proteus, Morgarella, Providencia,* and *yersinia*. For the production of ASA intermediates, preferred Enterobacteriaceae strains are those that are able to produce 2,5-diketo-D-gluconic acid from D-glucose or carbon sources which can be converted to D-glucose by the strain. Included in the family of Enterobacteriaceae which are able to produce 2,5-diketo-D-gluconic acid from D-glucose solutions are the genus *Erwinia, Enterobacter, Gluconobacter* and *Pantoea,* for example. Intermediates in the microbial pathway from carbon source to ASA, include but are not limited to GA, KDG, DKG, DKG, KLG, IA and EA. In the present invention, a preferred Enterobacteriaceae fermentation strain for the production of ASA intermediates is a *Pantoea* species and in particular, *Pantoea citrea*. Other Enterobacteriaceae strains that produce ASA intermediates include, but are not limited to, *E. Coli* and Gluconobacter.

As used herein the family "Bacillus" refers to rod-shaped bacterial strains having the general characteristics of being gram positive, capable of producing spores under certain environmental conditions.

As used herein, the term "recombinant" refers to a host cell that has a modification of its genome, e.g., as by the additional of nucleic acid not naturally occurring in the organism or by a modification of nucleic acid naturally occurring in the host cell and includes host cells having additional copies of endogenous nucleic acid introduced via recombinant means. The term "heterologous" as used herein refers to nucleic acid or amino acid sequences not naturally occurring in the host cell. As used herein, the term "endogenous" refers to a nucleic acid naturally occurring in the host.

The terms "isolated" or "purified" as used herein refer to an enzyme, or nucleic acid or protein or peptide or co-factor that is removed from at least one component with which it is naturally associated. In the present invention, an isolated nucleic acid can include a vector comprising the nucleic acid.

It is well understood in the art that the acidic derivatives of saccharides, may exist in a variety of ionization states depending upon their surrounding media, if in solution, or out of solution from which they are prepared if in solid form. The use of a term, such as, for example, idonic acid, to designate such molecules is intended to include all ionization states of the organic molecule referred to. Thus, for example, "idonic acid", its cyclized form "idonolactone", and "idonate" refer to the same organic moiety, and are not intended to specify particular ionization states or chemical forms.

As used herein, the term "vector" refers to a polynucleotide construct designed for transduction/transfection of one or more cell types including for example, "cloning vectors" which are designed for isolation, propagation and replication of inserted nucleotides or "expression vectors" which are designed for expression of a nucleotide sequence in a host cell, such as a *Pantoea citrea* or *E. coli* host cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) Nucleic Acids Res. 24: 1841–8; Chaturvedi et al. (1996) Nucleic Acids Res. 24: 2318–23; Schultz et al. (1996) Nucleic Acids Res. 24: 2966–73. A phosphorothioate linkage can be used in place of a phosphodiester linkage. Braun et al. (1988) J. Immunol. 141: 2084–9; Latimer et al. (1995) Molec. Immunol. 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, 95%, 97% or 99%) of "sequence identity" to another sequence means that, when aligned, that percentage of bases are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

A polynucleotide sequence that is "depicted in" a SEQ ID NO means that the sequence is present as an identical contiguous sequence in the SEQ ID NO. The term encompasses portions, or regions of the SEQ ID NO as well as the entire sequence contained within the SEQ ID NO.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Enzymatic Activities

Esters of phosphoric acid are encountered with trioses, tetroses, pentoses, hexoses and heptoses. The phosphorylation of all sugars is the initial step in their metabolism. Thus glucose can be phosphorylated to glucose 6-phospahte. All cells that can metabolize glucose contain some form of a hexokinase which catalyze the reaction

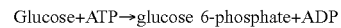

FIG. 9 depicts D-glucose and illustrates the "6th carbon". Exemplary hexokinases include hexokinase (Frohlich, et al., 1985, Gene 36:105–111) and glucokinase (Fukuda, et al., 1983, J. Bacteriol. 156:922–925). The DNA sequence of the glucokinase structural gene from *P. citrea* is shown in FIG. 4. The recogition site for the restriction enzymes NcoI (CCATGG) and SnaBi (TACGTA) are highlighted. FIG. 5 depicts the protein sequence of the glucokinase gene from *P. citrea*. Most hexokinases are somewhat nonspecific, showing some ability to catalyze formation of 6-phosphate esters of mannose, fructose, and galactose. In addition, other hexose derivatives may also be phosphorylated by a hexokinase. Gluconate (FIG. 3), for example, may also be phosphorylated by a kinase, specifically gluconokinase (citation). The sequence for the gluconokinase structural gene from *P. citrea* is depicted in FIG. 6. The recognition site for the restriction enzyme Pst I (CTGCAG) is highlighted. The protein sequence for the gluconokinase gene from *P. citrea* is depicted in FIG. 7 (SEQ ID NO 4). The some of the genes for glucokinase and gluconokinase (glk, gntk, etc.) are shown in FIG. 8.

FIG. 17 shows the interrelationships between the catabolic pathway and the oxidative pathway. Glucose can enter the catabolic pathway through the glycolytic pathway by the phosphorylation of glucose to glucose-6-phosphate by glucokinase (Glk); and through the pentose pathway by the phosphorylation of gluconate to gluconate-6-phosphate by glucono kinase (Gntk). Inactivation or modifying the levels of glucokinase and gluconokinase by modifying the nucleic acid or polypeptide encoding the same (glk and/or gntk), results in the increased yield of the desired product, e.g. an ascorbic acid intermediate. Genetic modifications are used to eliminate the communication between the catabolic functions and the enzymatic reactions that are required to synthesize a desired product. While glucokinase and gluconokinase are modified in one embodiment, the inventors contemplate that other enzymatic steps could be modified to achieve the same uncoupling oxidative, catabolic pathway uncoupling.

In another embodiment, the catabolic pathway is uncoupled from the productive pathway to increase the production of 5-KDG and/or tartrate. As shown in FIG. 21, glucose can enter the catabolic pathway through the glycolytic pathway, for example through glucose-6-phosphate, the pentose pathway through gluconate-6-phosphate, and other ascorbic acid by-products, such as idonate and 2-KLG. Inactivation or modifying the levels of glucokinase, gluconokinase, 2,5-DKG reductase, 5-keto-D-gluconate 5-reductase (idnO) and Idonate 5-dehydrogenase (idnD), by modifying the nucleic acid or polypeptide encoding the same, results in the increased yield of the desired product, e.g. 5-DKG and/or tartrate.

In another embodiment, the catabolic pathway is uncoupled from the productive pathway to increase the production of gluconate. As shown in FIG. 18 glucose can enter the catabolic pathway through the glycolytic pathway, for example through glucose-6-phosphate and the pentose pathway, through gluconate-6-phosphate. Inactivation or modifying the levels of glucokinase, gluconokinase, and glyceraldhehyde hydrogenase, by modifying the nucleic acid or polypeptide encoding the same, results in the increased yield of the desired product, e.g. gluconate.

In another embodiment, the catabolic pathway is uncoupled from the productive pathway to increase the production of erythorbic acid. As shown in FIG. 19 glucose can enter the catabolic pathway through the glycolytic pathway, for example through glucose-6-phosphate; the pentose pathway, through gluconate-6-phosphate; and by an enzymatic transport system transporting 2-KDG and 2,5-KDG into the cytoplasm. Inactivation or modifying the levels of glucokinase, gluconokinase, and 2-KDG hydrogenase; and the transport system of 2-KDG into the cytoplasm, by modifying the nucleic acid or polypeptide encoding the same, results in the increased yield of the desired product, e.g. erythoric acid.

In another embodiment, the catabolic pathway is uncoupled from the productive pathway to increase the production of 2,5-DKG. As shown in FIG. 20, glucose can enter the catabolic pathway through the glycolytic pathway, for example through glucose-6-phosphate; the pentose pathway, through gluconate-6-phosphate; and by an enzymatic transport system transporting 2-KDG and 2,5-KDG into the cytoplasm. Inactivation or modifying the levels of glucokinase, gluconokinase and 2-KDG hydrogenase; and the transport system of 2-KDG into the cytoplasm by modifying the nucleic acid or polypeptide encoding the same, results in the increased yield of the desired product, e.g. 2,5-DKG.

The availability of recombinant techniques to effect expression of enzymes in foreign hosts permits the achievement of the aspect of the invention which envisions production of an ascorbic acid intermediate with a reduced amount of carbon substrate diverted to catabolic pathways from a readily available carbon substrate. This method has considerable advantage over presently used methods in characterized by a reduction in the amount of substrate converted to the catabolic pathway and thus unavailable for conversion to the desired oxidative end-product, e.g., an ascorbic acid intermediate. This results in increased fermentative efficiency and increased yield over fermentations with wild type organisms. Certain wild type organisms may produce ascorbic acid intermediates, e.g., 2-KLG, however the level produced may not be sufficient to be economically practical. It has been observed that wild type *Pantoea citrea* has its own cytoplasmic glucokinase and gluconokinase enabling the organism to convert glucose to phosphorylated derivatives for use in its central metabolic pathways and the production of which, necessarily consume energy, ATP and causes that more carbon goes to non-2-KLG producing pathways. Under the same controlled conditions and using the method of this invention, described below, in two interruption plasmid described elsewhere in this application the glucokinase and gluconokinase genes can be deleted from the *P. citrea* genome, enabling the modified *P. citrea* to produce increased DKG from glucose at a a level increased over the wild-type, e.g.level of 63% yield to about 97–98% yield. [see Example 6].

One approach to producing a single organism conversion that is included in this invention comprises construction of an expression vector for the deleted kinase as outlined above, and transfer of this vector by any of the gene transfer methods mentioned above such as transformation, transduction or conjugation, into cells which are capable of the initial conversion of ordinary metabolites into the 2,5-DKG substrate for this enzyme. As outlined in the example below, this gene transfer results in a organism that is characterized by an increased yield of ascorbic acid intermediates. The details of the vector construction, gene transfer, and use of the resultant organism are described in the specification.

An alternative approach is to clone the genes encoding the enzymes known to effect the conversion of glucose or other ordinary metabolite to 2,5-DKG from the organisms known to contain them, to construct expression vectors containing these cloned gene sequences, and to transfer such vectors to cells which normally produce the 2,5-DKG reductase. Examples of the enzymes effecting the conversion of an ordinary metabolite to 2,5-DKG are D-glucose dehydrogenase (Adachi, O. et al., Agric. Biol. Chem., 44(2):301–308 [1980] Ameyama, M. et al., Agric. Biol. Chem. 45[4]: 851–861 [1981]), D-gluconate dehydrogenase (McIntire, W. et al., Biochem. J., 231:651–654 [1985]; Shinagawa, E. et al., Agric. Biol. Chem. 40[3]:475–483 [1976]; Shinagawa, E. et al., Agric. Biol. Chem. 42[5]:1055–1057 [1978]), 5-keto-D-gluconate dehydrogenase and 2-keto-D-gluconate dehydrogenase (Shinagawa, E. et al., Agric. Biol. Chem., 45(5):1079–1085 [1981]). A third approach is to transfer to a neutral host the entire sequence of enzymes comprising the conversion of an ordinary metabolite to 2-KLG. This last approach offers the advantage of choice of host organism almost at will, for whatever desirable growth characteristics and nutritional requirements it may have. Thus, the use as host cells of organisms which have the heritage of a reasonable history of experience in their culture and growth, such as *E. coli* and *Bacillus*, confers the advantage of uniformity with other procedures involving bacterial production of enzymes or substrates.

Once the organism capable of carrying out the conversion has been created, the process of the invention may be carried out in a variety of ways depending on the nature of the construction of the expression vectors for the recombinant enzymes and upon the growth characteristics of the host. Typically, the host organism will be grown under conditions which are favorable to production of large quantities of cells. When a large number of cells has accumulated, the promoter(s) supplied with the recombinant gene sequences either become or are already active, permitting the transcription and translation of the coding sequences. Upon suitable expression of these genes, and hence the presence of the desired catalytic quantities of enzyme, the starting material such as glucose, is added to the medium at a level of 1–500 g/L and the culture maintained at 20° C.° to about 40° C., preferably around 25°–37° C. for 1–300 hours until conversion to 2-KLG is effected. The starting material concentration may be maintained at a constant level through continuous feed control, and the 2-KLG produced is recovered from the medium either batchwise or continuously by means known in the art.

C. General Methods Involved in the Invention

In the examples below, the following general procedures were used in connection with probe construction, screening, hybridization of probe to desired material and in vector construction.

C.1 Isolation of Plasmids, Cleavage with Restriction Enzymes

Plasmids were isolated from the identified cultures using the cleared lysate method of Clewell, D. B. and Helinski, Biochemistry 9: 4428 (1970), incorporated herein by reference, and purified by column chromatography on Biorad A-50 Agarose. Smaller amounts (mini-preps) were prepared using the procedure of Birnboim, H. C. Nucleic Acids Research 7: 1513 (1979).

Fragments of the cloned plasmids were prepared for sequencing by treating about 20 .mu.g of plasmids with 10 to 50 units of the appropriate restriction enzyme or sequence of restriction enzymes in approximately 600 .mu.l solution containing the appropriate buffer for the restriction enzyme used or sequence of buffers; each enzyme incubation was at 37.degree. C. for one hour. After incubation with each enzyme, protein was removed and nucleic acids recovered by phenol-chloroform extraction and ethanol precipitation.

As shown in FIG. 1, there are multiple connections the catabolic, pentose and tricarboxylic acids (TCA) pathways. GDH=glucose dehydrogenase; GADH=gluconate dehydrogenase; 2-kDGH=2-keto-d-gluconate dehydrogenase; 2-KDG=2-keto-D-gluconate; IADH=idonate dehydrogenase; 2,5-DKG=2,5-diketogluconate; 2KLG=2-keto-L-gulonate; 5-KDG=5-keto-D-gluconate; 2KR=2-ketoreductase; 2,5DKGR=2,5-diketogluconate reductase; GlkA=glucokinase; GntK=gluconokinase; 5-KR=5-ketoreductase; 2,5-DKGR. As can be seen, the removal of the glucokinase activity blocks the entry of the glucose into the catabolic pathway, while the deletion of the gluconokinase activity does not allow the entry of gluconate into the pentose assimilatory pathway. From this scheme, it is evident that the absence of the glucokinase and/or gluconokinase activities should impair the metabolism of glucose and its oxidation products.

Production of ASA intermediates

The present invention provides methods for the production of ascorbic acid intermediates in host cells. The present invention encompasses methods wherein the levels of an enzymatic activity which phosphorylates D-glucose at its 6th carbon and/or the levels of an enzymatic activity which phosphorylates D-gluconate at its 6th carbon are decreased during part or all of the culturing. The present invention encompasses methods wherein the levels of an enzymatic activity which phosphorylates D-glucose at its 6th carbon and/or the levels of an enzymatic activity which phosphorylates D-gluconate at its 6th carbon are increased during part or all of the culturing. The present invention also encompasses a method wherein the levels of an enzymatic activity which phosphorylates D-glucose as its 6th carbon and/or the levels of an enzymatic activity which phosphorylates D-gluconate at its 6th carbon are not modified or are increased at the beginning of the culturing to facilitate growth, that is, to produce cell biomass, and decreased during the later phases of culturing to facilitate desired product accumulation.

The present invention provides a modified nucleic acid or polynucleotide that uncouples the oxidative pathway from the catabolic pathway in a host organism. In one embodiment the modified nucleic acid or polynucleotide lacks the encoding that expresses the phosphorylation of the desired substrate and thus inactivates the phosphorylating enzymatic activity.

The ASA intermediate may be further converted to a desired end product such as ASA or erythorbate. For the production of ASA intermediates, any host cell which is capable of converting a carbon source to DKG can be used. Preferred strains of the family Enterobacteriaceae are those that produce 2,5-diketo-D-gluconic acid from D-glucose solutions, including *Pantoea*, are described in Kageyama et al. (1992) International Journal of Systematic Bacteriology vol. 42, p. 203–210. In a preferred embodiment, the host cell is *Pantoea citrea* having a deletion of part or all of a polynucleotide that encodes an endogenous glucokinase (encoded by nucleic acid as depicted in SEQ ID NO:1) and a deletion of part or all of a polynucleotide that encodes an endogenous gluconokinase (encoded by nucleic acid as depicted in SEQ ID NO:3).

The production of ASA intermediates can proceed in a fermentative environment, that is, in an in vivo environment, or a non-fermentative environment, that is, in an in vitro environment; or combined in vivo/in vitro environments. In the methods which are further described infra, the host cell or the in vitro environment further comprise a heterologous genome which has the section encoding the phosphorylation activity, e.g. the glucokinase sequence and the gluconokinase sequence, inactivated.

A. In Vivo Biocatalytic Environment

The present invention encompasses the use of host cells comprising a modification in a polynucleotide encoding an endogenous enzymatic activity that phosphorylates D-glucose at its 6th carbon and/or a modification in a polynucleotide encoding an enzymatic activity that phosphorylates D-gluconate at its 6th carbon in the in vivo production of ASA intermediates. Biocatalysis begins with culturing the host cell in an environment with a suitable carbon source ordinarily used by Enterobacteriaceae strains, such as a 6 carbon sugar, for example, glucose, or a 6 carbon sugar acid, or combinations of 6 carbon sugars and/or 6 carbon sugar acids. Other carbon sources include, but are not limited to galactose, lactose, fructose, or the enzymatic derivatives of such. In addition to an appropriate carbon source, fermentation media must contain suitable minerals, salts, cofactors, buffers and other components, known to those of skill in the art for the growth of cultures and promotion of the enzymatic pathway necessary for production of desired end-products.

In one illustrative in vivo *Pantoea* pathway, D-glucose undergoes a series of membrane oxidative steps through enzymatic conversions, which may include the enzymes D-glucose dehydrogenase, D-gluconate dehydrogenase and 2-keto-D-gluconate dehydrogenase to give intermediates which may include, but are not limited to GA, KDG, and DKG, see FIG. 1. These intermediates undergo a series of intracellular reducing steps through enzymatic conversions, which may include the enzymes 2,5-diketo-D-gluconate reductase (DKGR), 2-keto reductase (2-KR) and 5-keto reductase (5-KR) to give end products which include but are not limited to KLG and IA. In a preferred embodiment of the in vivo environment for the production of ASA intermediates, 5-KR activity is deleted in order to prevent the consumption of IA. Other embodiments having other desired inactivated nucleic acid sections depending on the desired product and desired pathways to be inactivated.

If KLG is a desired intermediate, nucleic acid encoding DKGR is recombinantly introduced into the *Pantoea* fermentation strain. Many species have been found to contain DKGR particularly members of the Coryneform group, including the genera *Corynebacterium, Brevibacterium*, and *Arthrobacter*.

In some embodiments of the present invention, 2,5-DKGR from *Corynebacterium* sp. strain SHS752001 (Grindley et al., 1988, Applied and Environmental Microbiology 54: 1770–1775) is recombinantly introduced into a *Pantoea* strain. Production of recombinant 2,5 DKG reductase by *Erwinia herbicola* is disclosed in U.S. Pat. No. 5,008,193 to Anderson et al. Other sources of DKG reductase are provided in Table I.

The fermentation may be performed in a batch process or in a continuous process. In a batch process, regardless of what is added, all of the broth is harvested at the same time. In a continuous system, the broth is regularly removed for downstream processing while fresh substrate is added. The intermediates produced may be recovered from the fermentation broth by a variety of methods including ion exchange resins, absorption or ion retardation resins, activated carbon, concentration-crystallization, passage through a membrane, etc.

B. In Vitro Biocatalytic Environment

The invention provides for the biocatalytic production of ASA intermediates, e.g., KDG, DKG and KLG, from a carbon source in an in vitro or non-fermentative environment, such as in a bioreactor. The cells are first cultured for growth and for the non-fermentative process the carbon source utilized for growth is eliminated, the pH is maintained at between about pH 4 and about pH 9 and oxygen is present.

Depending upon the desired intermediate being produced, the process may require the presence of enzymatic co-factor. In a preferred embodiment disclosed herein, the enzymatic co-factor is regenerated. In some embodiments, KDG is the desired ASA intermediate produced, the bioreactor is provided with viable or non-viable *Pantoea citrea* host cells comprising a modification in a polynucleotide which normally encodes an endogenous enzymatic activity that phosphorylates D-glucose at its 6th carbon and/or a modification in a polynucleotide encoding an enzymatic activity that phosphorylates D-gluconate at its 6th carbon. In this embodiment, the host cell also has a mutation in a gene encoding glucokinase (glk) and gluconokinase (gntk) activity. In this embodiment, the carbon source is biocatalytically converted through two oxidative steps, to KDG, with a reduced loss of substrate, glucose or gluconate, to the catabolic pathway. In this embodiment, there is an increased yield in the desired intermediate relative the wild-type.

When DKG is the desired ASA intermediate, the bioreactor is provided with viable or non-viable *Pantoea citrea* host cells comprising a modification in a polynucleotide encoding an endogenous glucokinase and gluconokinase enzymatic activity that phosphorylates D-glucose at its 6th carbon and/or a modification in a polynucleotide encoding an enzymatic activity that phosphorylates D-gluconate at its 6th carbon and a carbon source which is biocatalytically converted through three oxidative steps, to DKG. In this embodiment, there is no need for co-factor regeneration.

When KLG is the desired ASA intermediate, the bioreactor is provided with viable or non-viable *Pantoea citrea* host cells comprising a modification in a polynucleotide which lacks the encoding or is unable to encode an endogenous enzymatic activity that diverts the glucose into the catabolic pathway, e.g., lacks the ability to phosphorylate D-glucose at its 6th carbon and/or a modification in a polynucleotide which lacks the encoding or is unable to encode an enzymatic activity that phosphorylates D-gluconate at its 6th carbon and a carbon source, such as D-glucose, which is biocatalytically converted through three oxidative steps, and one reducing step to KLG. In this embodiment, the reductase activity may be encoded by nucleic acid contained within the *Pantoea citrea* host cell or provided exogenously. In this embodiment, the first oxidative enzymatic activity requires an oxidized form of the co-factor and the reducing enzymatic activity requires a reduced form of co-factor. In a preferred embodiment disclosed herein, the *Pantoea citrea* cell is modified to eliminate the naturally occurring GDH activity and a heterologous GDH activity, such as one obtainable from *T. acidophilum, Cryptococcus uniguttalatus* or *Bacillus* species and having a specificity for NADPH+, is introduced into the *Pantoea* cell in order to provide a co-factor recycling system which requires and regenerates one co-factor. In this embodiment, the host cell further comprises nucleic acid encoding a 2,5-DKG reductase activity or the 2,5-DKG reductase is added exogenously to the bioreactor.

In another embodiment for making KLG, the bioreactor is charged with *Pantoea citrea* cells comprising a modification in nucleic acid encoding an endogenous enzymatic activity which phosphorylates D-glucose at its 6th carbon and/or in nucleic acid encoding an enzymatic activity that phosphorylates D-gluconate at its 6th carbon and further comprises nucleic acid encoding membrane-bound GDH, appropriate enzymes and cofactor, and D-gluconic acid is added which is converted to DKG. The reaction mixture is then made anaerobic and glucose is added. The GDH converts the glucose to GA, and the reductase converts DKG to KLG, while cofactor is recycled. When these reactions are completed, oxygen is added to convert GA to DKG, and the cycles continue.

In the in vitro biocatalytic process, the carbon source and metabolites thereof proceed through enzymatic oxidation steps or enzymatic oxidation and enzymatic reducing steps which may take place outside of the host cell intracellular environment and which exploit the enzymatic activity associated with the host cell and proceed through a pathway to produce the desired ASA intermediate. The enzymatic steps may proceed sequentially or simultaneously within the bioreactor and some have a co-factor requirement in order to produce the desired ASA intermediate. The present invention encompasses an in vitro process wherein the host cells are treated with an organic substance, such that the cells are non-viable, yet enzymes remain available for oxidation and reduction of the desired carbon source and/or metabolites thereof in the biocatalysis of carbon source to ASA intermediate.

The bioreactor may be performed in a batch process or in a continuous process. In a batch system, regardless of what is added, all of the broth is harvested at the same time. In a continuous system, the broth is regularly removed for downstream processing while fresh substrate is added. The intermediates produced may be recovered from the fermentation broth by a variety of methods including ion exchange resins, absorption or ion retardation resins, activated carbon, concentration-crystallization, passage through a membrane, etc.

In some embodiments, the host cell is permeabilized or lyophilized (Izumi et al., J. Ferment. Technol 61 (1983) 135–142) as long as the necessary enzymatic activities remain available to convert the carbon source or derivatives thereof while reducing the incorporation of portions of the carbon source or derivatives thereof into the catabolic pathway. The bioreactor may proceed with some enzymatic activities being provided exogenously and in an environment wherein solvents or long polymers are provided which stabilize or increase the enzymatic activities.

C. Host Cells Producing ASA

Any oxidative or reducing enzymes necessary for directing a host cell carbohydrate pathway into an ASA intermediate, such as, for example, KDG, DKG or KLG, can be introduced via recombinant DNA techniques known to those of skill in the art if such enzymes are not naturally occurring in the host cell. Alternatively, enzymes that would hinder an undesired catabolic pathway can be inactivated by recombinant DNA methods. The present invention encompasses the recombinant introduction or inactivation of any enzyme or intermediate necessary to achieve a desired pathway.

In some embodiments, Enterobacteriaceae strains that have been cured of a cryptic plasmid are used in the production of ASA, see PCT WO 98/59054.

In some embodiments, the host cell used for the production of an ASA intermediate is *Pantoea citrea,* for example, ATCC accession number 39140. Sources for nucleic acid encoding oxidative or reducing enzymes which can be used in the production of ASA intermediates in *Pantoea* species include the following:

TABLE I

| ENZYME | CITATION |
| --- | --- |
| glucose dehydrogenase | Smith et al. 1989, Biochem. J. 261:973; Neijssel et al. 1989, Antonie Van Leauvenhoek 56(1):51–61 |
| gluconic acid dehydrogenase | Matsushita et al. 1979, J. Biochem. 85:1173; Kulbe et al. 1987, Ann. N.Y. Acad Sci 6:552 |
| 2-keto-D-gluconic acid dehydrogenase | Stroshane 1977 Biotechnol. BioEng 19(4)459 |
| 2-keto gluconate reductase | J. Gen. Microbiol. 1991, 137:1479 |
| 2,5-diketo-D-gluconic acid reductase | U.S. Pat. Nos.: 5,795,761; 5,376,544; 5,583,025; 4,757,012; 4,758,514; 5,008,193; 5,004,690; 5,032,514 |

D. Recovery of ASA Intermediates

Once produced, the ASA intermediates can be recovered and/or purified by any means known to those of skill in the art, including, lyophilization, crystallization, spray-drying, and electrodialysis, etc. Electrodialysis methods for purifying ASA and ASA intermediates such as KLG are described in for example, U.S. Pat. No. 5,747,306 issued May 5, 1998 and U.S. Pat. No. 4,767,870, issued Aug. 30, 1998. Alternatively, the intermediates can also be formulated directly from the fermentation broth or bioreactor and granulated or put in a liquid formulation.

KLG produced by a process of the present invention may be further converted to ascorbic acid and the KDG to erythorbate by means known to those of skill in the art, see for example, Reichstein and Grussner, Helv. Chim. Acta., 17, 311–328 (1934). Four stereoisomers of ascorbic acid are possible: L-ascorbic acid, D-araboascorbic acid (erythorbic acid), which shows vitamin C activity, L-araboascorbic acid, and D-xyloascorbic acid.

E. Assay Conditions

Methods for detection of ASA intermediates, ASA and ASA stereoisomers include the use of redox-titration with 2,6 dichloroindophenol (Burton et al. 1979, J. Assoc. Pub. Analysts 17:105) or other suitable reagents; high-performance liquid chromatography (HPLC) using anion exchange (J. Chrom. 1980, 196:163); and electro-redox procedures (Pachia, 1976, Anal. Chem. 48:364). The skilled artisan will be well aware of controls to be applied in utilizing these detection methods.

Fermentation Media:

Fermentation media in the present invention must contain suitable carbon substrates which will include but are not limited to monosaccharides such as glucose, oligosaccharides such as lactose or sucrose, polysaccharides such as starch or cellulose and unpurified mixtures from a renewable feedstocks such as cheese whey permeate, cornsteep liquor, sugar beet molasses, and barley malt. Additionally the carbon substrate may also be one-carbon substrates such as carbon. While it is contemplated that the source of carbon utilized in the present invention may encompass a wide variety of carbon containing substrates and will only be limited by the choice of organism, the preferred carbon substrates include glucose and/or fructose and mixtures thereof. By using mixtures of glucose and fructose in combination with the modified genomes described elsewhere in this application, uncoupling of the oxidative pathways from the catabolic pathways allows the use of glucose for improved yield and conversion to the desired ascorbic acid intermediate while utilizing the fructose to satisfy the metalbolic requirements of the host cells.

Although it is contemplated that all of the above mentioned carbon substrates are suitable in the present invention preferred are the carbohydrates glucose, fructose or sucrose. The concentration of the carbon substrate is from about 55% to about 75% on a weight/weight basis. Preferably, the concentration is from about 60 to about 70% on a weight/weight basis. The inventors most preferably used 60% or 67% glucose.

In addition to an appropriate carbon source, fermentation media must contain suitable minerals, salts, vitamins, cofactors and buffers suitable for the growth or the cultures and promotion of the enzymatic pathway necessary for ascorbic acid intermediate production.

Culture Conditions:

Precultures:

Typically cell cultures are grown at 25 to 32 degree. C., and preferably about 28 or 29° C. in appropriate media. While the examples describe growth media used, other exemplary growth media useful in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science.

Suitable pH ranges preferred for the fermentation are between pH 5 to pH 8 where pH 7 to pH 7.5 for the seed flasks and between pH 5 to pH 6 for the reactor vessel.

It will be appreciated by one of skill in the art of fermentation microbiology that, now that Applicants have demonstrated the feasibility of the process of the present invention a number of factors affecting the fermentation processes may have to be optimized and controlled in order to maximize the ascorbic acid intermediate production. Many of these factors such as pH, carbon source concentration, and dissolved oxygen levels may affect the enzymatic process depending on the cell types used for ascorbic acid intermediate production.

Batch and Continuous Fermentations:

The present process employs a fed-batch method of fermentation for its culture systems. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for ascorbic acid intermediate production.

Identification and Purification of Ascorbic Acid Intermediates:

Methods for the purification of the desired ascorbic acid intermediate from fermentation media are known in the art.

The specific ascorbic acid intermediate may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

EXAMPLES

General Methods

Materials and Methods suitable for the maintenance and growth of bacterial cultures were found in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), pp. 210–213. American Society for Microbiology, Wash., DC. or Thomas D. Brock in Biotechnology: A Textbook of Industrial Microbiology, Second Edition (1989) Sinauer Associates, Inc., Sunderland, Mass. All reagents and materials used for the growth, and of bacterial cells were obtained from Diffco Laboratories (Detroit, Mich.), Aldrich Chemicals (Milwaukee, Wis.) or Sigma Chemical Company (St. Louis, Mo.) unless otherwise specified.

Growth medium for the precultures or inoculuum is commercially available and preparations such as Luria Bertani (LB) broth, Sabouraud Dextrose (SD) broth or Yeast medium (YM) broth are obtainable from GIBCO/BRL (Gaithersburg, Md.). LB-50 amp is Luria-Bertani broth containing 50 .mu.g/ml ampicillin.

Fermentation Media:

Two basic fermentation media were prepared for use in the following examples, and identified as Seed Flask Media and Fermentation Media. These basic media were modified by altering the carbon source or by the addition of other reagents such as sulfite. The reagents useful for the respective media include $KH_2PO_4$, $K_2HPO_4$, $MgSO4\ 7H_2O$, Difco Soytone, Sodium citrate, Fructose, $(NH_4)_2SO_4$, Nicotinic acid, $FeCl_3\ 6H_2O$, and trace salts, including, but not limited to $ZnSO_4\ 7H_2O$, $MnSO_4 H_2O$, and $Na_2MoO_4.2H_2O$); $KH_2PO_4$, $MgSO47H2O$, $(NH_4)_2SO_4$, Mono-sodium glutamate, $ZnSO_4\ 7H_2O$, $MnSO_4\ H_2O$, $Na_2MoO_4.2H_2O$, $FeCl_3\ 6H_2O$, Choline chloride, Mazu DF-204 (an antifoaming agent), Nicotinic acid, Ca-pantothenate and HFCS (42DE). HFCS can also be made according to the desired ratios of glucose to fructose, e.g., a frucose/glucose solution made of 27.3 g/L powdered fructose, 25.0 g/L powdered glucose.

Cells:

All commercially available cells used in the following examples were obtained from the ATCC and are identified in the text by their ATCC number. Recombinant *P. citrea* cells (ATCC39140) were used as ascorbic acid intermediate producers and were constructed as described in Examples 4 and 5. Enzymatic assays and genome analysis revealed that the strains MDP41 and DD6 lacked the genes encoding the glucokinase, gluconokinase and both enzymes whereas the wild-type strains contained genes encoding the glucokinase and/or gluconokinase enzymes.

Ascorbic Acid Intermediate Analysis:

The presence of ascorbic acid intermediates, e.g., 2-KLG, was verified by running a HPLC analysis. Fermentation reactor vessel samples were drawn off the tank and loaded onto Dionex (Sunnyvale, Calif., Product No. 043118) Ion Pac AS 10 column (4 mm times 250 mm) connected to a Waters 2690 Separation Module and a Waters 410 Differential Refractometer (Milford, Mass.).

Methods of Assaying for Production of Ascorbic Acid Intermediate

Methods for determining the yield, OUR, and CER were described earlier in the definition section.

Recombinant methods

Vector sequences

Expression vectors used the methods of the present invention comprise at least one promoter associated with the enzyme, which promoter is functional in the host cell. In one embodiment of the present invention, the promoter is the wild-type promoter for the selected enzyme and in another embodiment of the present invention, the promoter is heterologous to the enzyme, but still functional in the host cell. In one embodiment of the present invention, nucleic acid encoding the enzyme is stably integrated into the microorganism genome.

In some embodiments, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host microorganism which allows for ease of selection of those hosts containing the vector. Examples of such selectable markers include but are not limited to antibiotics, such as, erythromycin, actinomycin, chloramphenicol and tetracycline.

A preferred plasmid for the recombinant introduction of non-naturally occurring enzymes or intermediates into a strain of Enterobacteriaceae is RSF1010, a mobilizable, but not self transmissible plasmid which has the capability to replicate in a broad range of bacterial hosts, including Gram− and Gram+ bacteria. (Frey et al., 1989, The Molecular biology of IncQ plasmids. In: Thomas (Ed.), *Promiscuous Plasmids of Gram Negative Bacteria*. Academic Press, London, pp. 79–94). Frey et al. (1992, Gene 113:101–106) report on three regions found to affect the mobilization properties of RSF1010.

Transformation

General transformation procedures are taught in Current Protocols In Molecular Biology (vol. 1, edited by Ausubel et al., John Wiley & Sons, Inc. 1987, Chapter 9) and include calcium phosphate methods, transformation using DEAE-Dextran and electroporation. A variety of transformation procedures are known by those of skill in the art for introducing nucleic acid encoding a desired protein in a given host cell. A variety of host cells can be used for recombinantly producing the pathway enzymes to be added exogenously, including bacterial, fungal, mammalian, insect and plant cells.

In some embodiments of the process, the host cell is an Enterobacteriaceae. Included in the group of Enterobacteriaceae are Erwinia, Enterobacter, Gluconobacter and *Pantoea* species. In the present invention, a preferred Enterobacteriaceae fermentation strain for the production of ASA intermediates is a *Pantoea* species and in particular, *Pantoea citrea*. In some embodiments, the host cell is *Pantoea citrea* comprising pathway enzymes capable of converting a carbon source to KLG.

Identification of Transformants

Whether a host cell has been transformed can be detected by the presence/absence of marker gene expression which can suggest whether the nucleic acid of interest is present However, its expression should be confirmed. For example, if the nucleic acid encoding a pathway enzyme is inserted within a marker gene sequence, recombinant cells containing the insert can be identified by the absence of marker gene function. Alternatively, a marker gene can be placed in tandem with nucleic acid encoding the pathway enzyme under the control of a single promoter. Expression of the marker gene in response to induction or selection usually indicates expression of the enzyme as well.

Alternatively, host cells which contain the coding sequence for a pathway enzyme and express the enzyme may be identified by a variety of procedures known to those of skill in the art. These procedures include, but are not limited to, DNA—DNA or DNA-RNA hybridization and protein bioassay or immunoassay techniques which include membrane-based, solution-based, or chip-based technologies for the detection and/or quantification of the nucleic acid or protein.

Additionally, the presence of the enzyme polynucleotide sequence in a host microorganism can be detected by DNA—DNA or DNA-RNA hybridization or amplification using probes, portions or fragments of the enzyme polynucleotide sequences.

The manner and method of carrying out the present invention may be more fully understood by those of skill in the art by reference to the following examples, which examples are not intended in any manner to limit the scope of the present invention or of the claims directed thereto. All references and patent publications referred to herein are hereby incorporated by reference.

EXAMPLES

Example 1

Construction of a Genomic Library from *P. citrea* 139-2a

*P. citrea* genomic DNA was prepared using the DNA-Pure TM genomic DNA Isolation Kit (CPG, Lincoln Park, N.J.). 50 micrograms of this DNA was partially digested with the restriction enzyme Sau3A accordingly the manufacturer recommendations (Roche Molecular Biochemicals, Indianapolis, Ind.). The products of the digestion were separated on a 1% agarose gel and the DNA fragments of 3–5 kilobases were purified from the gel using the Qiaquick Gel extraction kit (Qiagen Inc. Valencia, Calif.). The resulting DNA was ligated with BamH1-linearized plasmid pBK-CMV (Stratagene, La Jolla, Calif.). A library of around 10×× different plasmids was obtained in this way.

Example 2

Isolation of the Structural Gene for the Glucokinase Enzyme

To select for a plasmid that carries the glucokinase gene from *P. citrea*, the genomic library (see above) was transformed into a *E. coli* strain devoid of the glucokinase gene (glka) and the PTS transport system, strain NF9, glk⁻, (Flores et al., Nat. Biotech. 14, 620–623). After transformation, the cells were selected for growth on M9 media with glucose as the only carbon source. With this strategy, plasmids able to complement the glk⁻ or pts⁻ mutations were selected.

After 48 hrs. of incubation at 37° C., many colonies were visible. Several of these colonies were further purified and their plasmids isolated and characterized by restriction analysis. It was found that all the plasmids contained a common DNA fragment.

After re-transforming these plasmids back into NF9, glk⁻, all of them allowed growth on M9-glucose media, corroborating that they were able to complement at least one of the mutations present in NF9, glk⁻.

Plasmid pMD4 was isolated in this way and contains an insert of around 3.9 kb. The insert in this plasmid was sequenced and it was found that in a region of around 1010 bp, a gene with a strong similarity to the *E. coli* glkA gene was present. (SEQ ID 4.)

Example 3

Inactivation of the Glucokinase Gene by Homologous Recombination

The general strategy to inactivate genes by homologous recombination with a a suicide vector has been delineated before (Miller and Mekalanos., J. Bacteriol. 170 (1988) 2575–2583). To inactivate the glk gene from *P. citrea* by this approach two plasmids were constructed: pMD5 and pMD6.

To construct pMD5, plasmid pMD4 was digested with the NcoI and SnaB1 restriction enzymes accordingly manufacturer specifications. (Roche Molecular Biochemicals, Indianapolis, Ind.). The cohesive ends generated by these enzymes were blunt-ended with T4 polymerase using standard techniques. This DNA was ligated with a loxP-Cat-loxP cassette isolated from pLoxCat2 as a SpeI-EcoRV DNA fragment. (Palmeros et al., Gene (2000) 247, 255–264.). This cassette codes for Chloramphenicol resistance. The ligation mixture was transformed into TOP10 competent cell (Invitrogen, Carlsbard Calif.). selecting for growth on Chloramphenicol 10 micrograms/ml. Several colonies were obtained after 18 hr. incubation at 37° C. The plasmids of some of these colonies were purified and characterized by restriction analysis. The presence of the loxP-Cat-loxP and the deletion of the DNA region between the NcoI and SnaB1 sites in the glk gene was confirmed. The plasmid with these properties was named pMD5.

To construct pMD6, plasmid pMD5 was digested with the BamH1 and Cell11 restriction enzymes. The DNA fragment containing the glk gene interrupted with the loxP-cassette was ligated to a EcoRV-Bsa1 DNA fragment isolated from plasmid pR6Kori1 (unpublished results). This fragment contains the R6K origin of replication and the Kanamycin resistance gene. The ligation mixture was transformed into strain SY327 (Miller and Mekalanos., ibid.) and transformants were selected on plates containing kanamycin and chloramphenicol (20 and 10 micrograms/ml respectively). Several colonies were obtained after 24 hr. incubation at 37° C. The plasmids of some of these colonies were purified and characterized by restriction analysis. The presence of the loxP-Cat-loxP and the R6K origin was confirmed. The plasmid with these characteristics was named pMD6.

One characteristic of pMD6 and R6K derivatives in general, is that they can only replicate in strains that carry the pir gene from plasmid R6K (Miller and Mekalanos., ibid.). *P. citrea* does not contain the pir gene or sustains replication of pMD6. After transforming pMD6 into *P. citrea* 139-2a and selecting for Cm (R) strains, the proper gene replacement by homologous recombination was obtained. The inactivation of the glucokinase gene was confirmed by assaying Glucokinase activity using the glucokinase-glucose-6-phosphate deydrogenase coupled assay described by Fukuda et al., (Fukuda Y., Yamaguchi S., Shimosaka M., Murata K. and Kimura A. J. Bacteriol. (1983) vol. 156: pp. 922–925). The *P. citrea* strain where the glucokinase inactivation was confirmed was named MDP4.

Further confirmation of the inactivation of the glucokinase gene was generated by comparing the size PCR products obtained using chromosomal DNA from 139-2a or MDP4 strains and primers that hybridize with the glucokinase structural gene (SEQ. ID NO: 8 and 9, respectively). With this approach, the size of the PCR products should reflect that the loxP-Cat-loxP cassette was cloned in the glucokinase structural gene.

Example 4

Removal of the Chloramphenicol Resistance Marker in MDP4

After overnight growth on YENB medium (0.75% yeast extract, 0.8% nutrient broth) at 30° C., *P. citrea* MDP40 in a water suspension was electrotransformed with plasmid pJW168 (. (Palmeros et al., Gene (2000) 247, 255–264.). which contained the bacteriophage P1 Cre recombinase gene (IPTG-inducible), a temperature-sensitive pSC101 replicon, and an ampicillin resistance gene. Upon outgrowth in SOC medium at 30° C., transformants were selected at 30° C. (permissive temperature for pJW168 replication) on LB agar medium supplemented with carbenicillin (200 µg/ml) and IPTG (1 mM). Two serial overnight transfers of pooled colonies were carried out at 35° C. on fresh LB agar medium supplemented with carbenicillin and IPTG in order to allow excision of the chromosomal chloramphenicol resistance gene via recombination at the loxP sites mediated by the Cre recombinase (Hoess and Abremski, J. Mol. Biol., 181: 351–362). Resultant colonies were replica-plated on to LB agar medium supplemented with carbenicillin and IPTG and LB agar supplemented with chloramphenicol (12.5 µg/ml) to identify colonies at 30° C. that were carbenicillin-resistant and chloramphenicol-sensitive indicating marker gene removal. An overnight 30° C. culture of one such colony was used to inoculate 10 ml of LB medium. Upon growth at 30° C. to OD (600 nm) of 0.6, the culture was incubated at 35° C. overnight. Several dilutions were plated on prewarmed LB agar medium and the plates incubated overnight at 35° C. (the non-permissive temperature for pJW168 replication). Resultant colonies were replica-plated on to LB agar medium and LB agar medium supplemented with carbenicillin (200 µg/ml) to identify colonies at 30° C. that were carbenicillin-sensitive, indicating loss of plasmid pJW168. One such glK mutant, MDP41, was further analyzed by genomic PCR using primers SEQ ID NO:5 and SEQ ID NO:6 and yielded the expected PCR product (data not shown).

Example 5

Inactivation of the Gluconate Kinase Gene by Homologous Recombination

The general strategy utilized to inactivate the gluconate kinase gene of *P. citrea* is presented in FIG. 10, was in essence the same used to inactivate the glucokinase gene as described in example 3. Briefly, after isolating and sequencing a plasmid that allowed a *E. coli* strain gntK⁻, idnK⁻, to grow using gluconate as the only carbon source (data not shown); a DNA fragment containing the structural gene for the gluconate kinase gene was generated by PCR using primers SEQ. ID NO: 7 and SEQ. ID NO: 8. This approximately 3 kb PCR product was cloned in a multicopy plasmid containing an R6K origin of replication. A unique PstI restriction site located in the gluconate kinase structural gene as shown in SEQ. ID NO: 2, was utilized to insert a loxP-Cat-loxP cassette. This construction was transferred to the chromosome of the *P. citrea* strain MDP41 by homologous recombination.

The correct interruption of the gluconate kinase with the loxP-Cat-loxP cassette was confirmed by PCR, using primers SEQ ID NO: 8 and SEQ ID NO: 9.

The new strain, with both glucose and gluconate kinase inactivated was named MDP5. This strain still contains the Cat marker inserted in the gluconate kinase structural gene. By repeating the procedure described in example 4, a marker-less strain was obtained and named DD6.

Experimental 6

The following illustrates the benefit of a double delete host cell (glucokinase and gluconokinase deleted *Pantoea* host cells) in terms of $O_2$ demand.

Seed Train:

A vial of culture stored in liquid nitrogen is thawed in air and 0.75 mL is added to a sterile 2-L Erlenmeyer flasks containing 500 mL of seed medium. Flasks are incubated at 29° C. and 250 rpm for 12 hours. Transfer criteria is an $OD_{550}$ greater than 2.5.

Seed flask medium

A medium composition was made according to the following:

| Component | Amount | |
|---|---|---|
| $KH_2PO_4$ | 12.0 g/L | |
| $K_2HPO_4$ | 4.0 g/L | |
| MgSO4 7$H_2O$ | 2.0 g/L | |
| Difco Soytone | 2.0 g/L | |
| Sodium citrate | 0.1 g/L | |
| Fructose | 5.0 g/L | |
| $(NH_4)_2SO_4$ | 1.0 g/L | |
| Nicotinic acid | 0.02 g/L | |
| $FeCl_3$ 6$H_2O$ | 5 mL/L | (of a 0.4 g/L stock solution) |
| Trace salts | 5 mL/L | (of the following solution: 0.58 g/L $ZnSO_4$ 7$H_2O$, 0.34 g/L $MnSO_4$ $H_2O$, 0.48 g/L $Na_2MoO_4 \cdot 2H_2O$) |

The pH of the medium solution was adjusted to 7.0±0.1 unit with 20% NaOH. Tetracycline HCl was added to a final concentration of 20 mg/L (2 mL/L of a 10 g/L stock solution). The resulting medium solution was then filter sterilized with a 0.2μ filter unit. The medium was then autoclaved and 500 mL of the previously autoclaved medium was added to 2-L Erlenmeyer flasks.

Production Fermentor
Additions to the reactor vessel prior to sterilization

| Component | Conc |
|---|---|
| $KH_2PO_4$ | 3.5 g/L |
| MgSO4 7H2O | 1.0 g/L |
| $(NH_4)_2SO_4$ | 0.92 g/L |
| Mono-sodium glutamate | 15.0 g/L |
| $ZnSO_4$ 7$H_2O$ | 5.79 mg/L |
| $MnSO_4$ $H_2O$ | 3.44 mg/L |
| $Na_2MoO_4 \cdot 2H_2O$ | 4.70 mg/L |
| $FeCl_3$ 6$H_2O$ | 2.20 mg/L |
| Choline chloride | 0.112 g/L |
| Mazu DF-204 | 0.167 g/L |

The above constituted media was sterilized at 121° C. for 45 minutes.

After tank sterilization, the following additions were made to the fermentation tank:

| Component | Conc |
|---|---|
| Nicotinic acid | 16.8 mg/L |
| Ca-pantothenate | 3.36 mg/L |
| HFCS (42DE) | 95.5 g/L (gluconate or glucose if desired as the particular starting substrate) |

The final volume after sterilization and addition of post-sterilization components was 6.0 L. The so prepared tank and medium were inoculated with the full entire contents from seed flask prepared as described to give a volume of 6.5 L.

Growth conditions were at 29° C. and pH 6.0. Agitation rate, back pressure, and air flow are adjusted as needed to keep dissolved oxygen above zero.

Results

The oxidative pathway for ascorbic acid intermediates is depicted in FIG. 10. By determining the amount of carbon dioxide produce (CER), one can calculate the amount of carbon utilized by the catabolic pathway and thus measure the uncoupling of the catabolic and productive (oxidative) pathways since the sole source of carbon for CO2 is from the carbon substrate, no additional CO2 having been supplied into the reactor vessel. When the wild-type organism was utilized in the fermentation process, 63% of the glucose was converted to an ascorbic acid intermediate, while 37% was converted, as measured by the CER, to catabolic products (FIG. 12). In the second phase of the study, the nucleic acid encoding glucokinase expression was run under conditions of the wild-type. As shown in FIG. 13A, CO2 evolution decreased to about 18%, as measured by CER. Thus glucose catabolism was reduced, but not completely uncoupled. In an attempt to ascertain the source, i.e. the pathway wherein the carbon substrate was being diverted to the catabolic pathway, gluconic acid was provided as the sole carbon source. As shown in FIG. 13B in comparison with FIG. 13A, gluconic acid was catabolized at about the same rate as if glucose had been the carbon substrate. (83% gluconate converted to ascorbic acid intermediate v. 17% of the gluconic acid converted to the catabolic pathway (as measured by CER). See also Table 2:

TABLE 2

| strain | Fraction of Glucose converted to | | Fraction of Gluconate converted to | |
| --- | --- | --- | --- | --- |
| | Metabolism | DKG | Metabolism | DKG |
| Wild-type | 0.37 | 0.63 | — | — |
| Glucokinase delete (glkA) | 0.18 | 0.82 | 0.17 | 0.83 |
| Gluconokinase delete (gntK) | 0.24 | 0.76 | 0.02 | 0.98 |

A last phase of the study was provided by the examination of the OUR and CER of a host cell having the genomic encoding for glucokinase and gluconokinase deleted from the host cell genome. FIG. 14 depicts 3% glucose was converted to CO2, wereas a control (wild-type) exhibited a 43% glucose to CO2 yield. As a result, it appears that the wild-type exhibited a high catabolism of glucose by the catabolic pathway, which resulted in reduced yield and a high oxygen requirement. However, a dual deletion of glucokinase and gluconokinase essentially inactivated catabolism to less than 10 percent, less than 5 per cent and particularly 3 or less % of the initial carbon substrate.

Conclusions

The double mutant of glucokinase and gluconokinase appeared to shunt almost all of the glucose to 2,5-DKG, about 98%.

Example 7

Production of Glycerol from Fructose.

To demonstrate that *Pantoea citrea* can be used to produce chemical compounds derived from fructose, glycerol was produced using the approach described by Empatage et al., [Emptage, M., Haynie, S., Laffend, L., Pucci, J. and Whited, G. Process for the biological production of 1,3-propanediol with high titer. Patent: WO 0112833-A 41 22 Feb. 2001; E.I. DU PONT DE NEMOURS AND COMPANY; GENENCOR INTERNATIONAL, INC.]. Briefly, this approach uses two enzymes from yeast to convert dihydroxyacetone phosphate (DHAP) into glycerol as shown in the reaction depicted in FIG. 25.

The genes for the GPD1 and GPP2 enzymes were cloned in a multicopy plasmid pTrc99 under the control of the Trc promoter (Empatage et al., 2001). This plasmid (pAH48) is able to produce high levels of both enzymes. The inventors recognized that to produce glycerol in *P. citrea*, it was desireable to eliminate or reduce the natural ability of the strain to assimilate glycerol. A common glycerol catabolic pathway in many bacteria, is through the action of the glycerol kinase [Lin E. C. Ann. Rev. Microbiol. 1976. 30:535–578. Glycerol dissimilation and its regulation in bacteria]. The inventors found that the *P. citrea* was able to grow in media containing glycerols as the only carbon source. Furthermore, inspection of the *P. citrea* genome sequence, showed that it possesses a glycerol kinase gene, very similar to the glkA gene from *E. coli*.

Thus, to eliminate the glycerol kinase activity, the structural gene of this enzyme (gene glpK) was inactivated. This was accomplished as described in Examples 3 and 5 (inactivation of glucokinase and gluconokinase genes). Briefly, a 2.9 kb DNA fragment containing the glpK gene and flanking sequences, was obtained by PCR using chromosomal DNA from *P. citrea* and the primers disclosed in SEQ ID NO: 11 and SEQ ID NO: 12. This 2.9 kb DNA fragment was cloned in a R6K vector as indicated in Examples 3 and 5. The DNA sequence of the glpK gene is shown in SEQ ID NO: 13, and the protein sequence of GlpK is shown in SEQ ID NO: 14. Inspection of the glpK DNA sequence showed the presence of a Hpa1 site, which was chosen to insert the LoxP-Cat-LoxP cassette. Once the desired plasmid construction was obtained, the glpK interruption was transferred to the chromosome of *P. citrea* strain 139-2a ps-, by homologous recombination as described in example 3 and 5. The resulting *P. citrea* glpK:: Cm strain was named MDG1.

Once the interruption of the glpK gene in the *P. citrea* genome was confirmed, the effect of this mutation was evaluated. For such a purpose, strain MDG1 was grown in minimal media M9 containing glycerol 0.4% as the only carbon source. After incubating the cells for 48 hours at 30° C., no growth was observed, indicating that strain MDG1 lost the ability to utilize glycerol as a carbon source.

Strain MDG1 was transformed with plasmid pAH48 (Emptage et al., 2001), and the resulting strain MDG2, was tested for its capacity to produce glycerol using fructose as the only carbon source. This was accomplished by incubating the strain in minimal media containing 2% fructose as the only carbon source. After incubating the cells for 24 hours at 30° C., a sample was collected and analyzed by HPLC as described by Emptage et al. (2001). By doing this, it was found that strain MDG1 did not produce any glycerol, while strain MDG2 produced 1.36 g/L of glycerol. These results demonstrated that *P. citrea* was able to divert a substantial part of fructose into the formation of glycerol.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

SEQUENCE LISTING

```
<160> NUMBER OF SEQ ID NOS: 14

<210> SEQ ID NO 1
<211> LENGTH: 963
<212> TYPE: DNA
<213> ORGANISM: Pantoea citrea
```

<400> SEQUENCE: 1

```
atgacaaact atgccttggt cggcgatgta ggcggaacta cgcccgcct tgcgttgtgt      60
gatgtgactg acggcagcat ctcgcaggcc aaaacctttt caaccgagga ttaccagagc    120
ctggaagatg ttattcgtga gtatctggcg atcaacaag ccatcacctg tgcatctatc    180
gccatcgcct gtccggtgaa agatgactgg attgaaatga ctaatcatag ctgggcgttc    240
tctatcagtg agatgaaaca aaatctcggg ctggaacatc tggaagtgat taacgatttc    300
actgcggtct ccatggcaat tccaatgctg gcagtgacg atgtcattca gttcggcggt    360
ggtgcaccgg taaagataa accgatagct atctatggtg ccggaacagg actgggggtg    420
agccatctgg ttcatgtcaa caaacactgg gtcagcttgc ctggtgaagg cggacatgta    480
gatttcacct gtggtaccga agaagaagac atgatcatga gtgtgctgcg tgcagaacgt    540
ggccgggtgt cagctgaacg ggtgctgtca ggaaaaggtc tggtgaatat ttaccgggcc    600
attgtgattt ctgacaaccg tgttcctgaa cgtctgcaac tcaggacgt aaccgagcgt    660
gcattatccg gaagctgtac tgactgtcgt cgtgcactgt cattgttctg tgtgattatg    720
ggacgttttg gcgggaacct ggccctgaca cttggaaccct tcggtggggt gtatattgcc    780
ggcggaattg ttccacgctt cctgcagttc tttaaagcct ccggtttccg tgctgctttc    840
gaagataagg gacgtttccg ttcttacgta caggatattc cggtctatct gattacccat    900
gatcagccgg ggctgctggg tgccggtgcc catatgcgcc agactttagg gatggaactg    960
taa                                                                 963
```

<210> SEQ ID NO 2
<211> LENGTH: 320
<212> TYPE: PRT
<213> ORGANISM: Pantoea citrea

<400> SEQUENCE: 2

```
Met Thr Asn Tyr Ala Leu Val Gly Asp Val Gly Gly Thr Asn Ala Arg
 1               5                  10                  15

Leu Ala Leu Cys Asp Val Thr Asp Gly Ser Ile Ser Gln Ala Lys Thr
            20                  25                  30

Phe Ser Thr Glu Asp Tyr Gln Ser Leu Glu Asp Val Ile Arg Glu Tyr
        35                  40                  45

Leu Ala Asp Gln Gln Ala Ile Thr Cys Ala Ser Ile Ala Ile Ala Cys
    50                  55                  60

Pro Val Lys Asp Asp Trp Ile Glu Met Thr Asn His Ser Trp Ala Phe
65                  70                  75                  80

Ser Ile Ser Glu Met Lys Gln Asn Leu Gly Leu Glu His Leu Glu Val
                85                  90                  95

Ile Asn Asp Phe Thr Ala Val Ser Met Ala Ile Pro Met Leu Gly Ser
            100                 105                 110

Asp Asp Val Ile Gln Phe Gly Gly Gly Ala Pro Val Lys Asp Lys Pro
        115                 120                 125

Ile Ala Ile Tyr Gly Ala Gly Thr Gly Leu Gly Val Ser His Leu Val
    130                 135                 140

His Val Asn Lys His Trp Val Ser Leu Pro Gly Glu Gly Gly His Val
145                 150                 155                 160

Asp Phe Thr Cys Gly Thr Glu Glu Asp Met Ile Met Ser Val Leu
                165                 170                 175

Arg Ala Glu Arg Gly Arg Val Ser Ala Glu Arg Val Leu Ser Gly Lys
            180                 185                 190
```

```
Gly Leu Val Asn Ile Tyr Arg Ala Ile Val Ile Ser Asp Asn Arg Val
            195                 200                 205

Pro Glu Arg Leu Gln Pro Gln Asp Val Thr Glu Arg Ala Leu Ser Gly
            210                 215                 220

Ser Cys Thr Asp Cys Arg Arg Ala Leu Ser Leu Phe Cys Val Ile Met
225                 230                 235                 240

Gly Arg Phe Gly Gly Asn Leu Ala Leu Thr Leu Gly Thr Phe Gly Gly
            245                 250                 255

Val Tyr Ile Ala Gly Gly Ile Val Pro Arg Phe Leu Gln Phe Phe Lys
            260                 265                 270

Ala Ser Gly Phe Arg Ala Ala Phe Glu Asp Lys Gly Arg Phe Arg Ser
            275                 280                 285

Tyr Val Gln Asp Ile Pro Val Tyr Leu Ile Thr His Asp Gln Pro Gly
            290                 295                 300

Leu Leu Gly Ala Gly Ala His Met Arg Gln Thr Leu Gly Met Glu Leu
305                 310                 315                 320

<210> SEQ ID NO 3
<211> LENGTH: 531
<212> TYPE: DNA
<213> ORGANISM: Pantoea citrea

<400> SEQUENCE: 3
atgagtacag cttcttcaaa tcatcatgtg tttatcctga tgggcgtttc cggcagcgga      60
aagtcggtgg tcgccaatcg tgtctcttac cagttgcaaa ccgcatttct tgatggtgac     120
tttctgcatc ccagagcgaa catcatgaaa atggctgacg gcatccgctc aatgatcag     180 gatcgtcaac cctggctgca ggccattaat gatgcggctt ttgctatgca gcggacccag     240
gctgtatcgt taattgtgtg ttcgtcactg aaaaaaagtt atcgcgatat tcttcgtgaa     300
ggtaacagca atcttaagtt tgtttatctg aaaggtgact tcgataccat cgaatcgcgt     360
cttaaagccc gcaagggaca cttcttcaaa cccgccatgc tggtaacaca attcgcaact     420
ctcgaagagc cgaccccgga tgaaactgat gtcctcacgg tggatatccg gcagtcgctg     480
gatgaggttg ttgctgccac ggtagaagcg atcaaacacg caattcagta a             531

<210> SEQ ID NO 4
<211> LENGTH: 176
<212> TYPE: PRT
<213> ORGANISM: Pantoea citrea

<400> SEQUENCE: 4

Met Ser Thr Ala Ser Ser Asn His His Val Phe Ile Leu Met Gly Val
1               5                   10                  15

Ser Gly Ser Gly Lys Ser Val Val Ala Asn Arg Val Ser Tyr Gln Leu
            20                  25                  30

Gln Thr Ala Phe Leu Asp Gly Asp Phe Leu His Pro Arg Ala Asn Ile
            35                  40                  45

Met Lys Met Ala Asp Gly His Pro Leu Asn Asp Gln Asp Arg Gln Pro
        50                  55                  60

Trp Leu Gln Ala Ile Asn Asp Ala Ala Phe Ala Met Gln Arg Thr Gln
65                  70                  75                  80

Ala Val Ser Leu Ile Val Cys Ser Ser Leu Lys Lys Ser Tyr Arg Asp
            85                  90                  95

Ile Leu Arg Glu Gly Asn Ser Asn Leu Lys Phe Val Tyr Leu Lys Gly
            100                 105                 110
```

```
Asp Phe Asp Thr Ile Glu Ser Arg Leu Lys Ala Arg Lys Gly His Phe
        115                 120                 125

Phe Lys Pro Ala Met Leu Val Thr Gln Phe Ala Thr Leu Glu Glu Pro
    130                 135                 140

Thr Pro Asp Glu Thr Asp Val Leu Thr Val Asp Ile Arg Gln Ser Leu
145                 150                 155                 160

Asp Glu Val Val Ala Ala Thr Val Glu Ala Ile Lys His Ala Ile Gln
                165                 170                 175

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ttttcaaccg aggattacca gagc                                        24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
cacggcgcag gaatgataca gaga                                        24

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gggaaggttc tgatgtgtcc gtg                                         23

<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
gccggttgca gcgcgtgacc gc                                          22

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
actaaaaggg tacggtgtca gaga                                        24

<210> SEQ ID NO 10
<211> LENGTH: 24
<212> TYPE: DNA
<213> ORGANISM: Artificial Sequence
<220> FEATURE:
```

<223> OTHER INFORMATION: primer

<400> SEQUENCE: 10
gtgttgcggt acttatcatt atta                                           24

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
tgcagtttca atgggtgttt a                                              21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tgtccggcat gcaggtcaga                                                20

<210> SEQ ID NO 13
<211> LENGTH: 1518
<212> TYPE: DNA
<213> ORGANISM: Pantoea citrea

<400> SEQUENCE: 13
atgactaacg ctgaaaacaa atacattgtt gcactggacc agggaaccac cagctcacga      60
gcggtagtac tggatcacga tgcaaatatt atcgcggttt cacaacgtga atttactcag     120
cactatccta aaacaggctg ggttgagcat gacccgatgg atatctgggc aacccagagt     180
tcaactctgg tagaagtact ggcacacgcc gatattcgtt ctgatcagat tgcggcgatt     240
ggtattacta accagcgtga aaccaccatc gtctgggata gaaaaccgg caagcctgtc      300 tataacgcaa ttgtctggca ggacccacgc accgctgact actgctcaaa actgaaaaaa     360
gaaggtcttg aagaatatat tcagaagacg accgggcttg tgattaaccc ttacttctcc     420
ggaaccaaaa taaaatggat tctggacaat gtggaaggtg cccgggatcg agccaaacgt     480
ggggaactgt tatttggtac cgttgacacc tggctggtct ggaaaatgac tcagggtcgt     540
gtgcatgtta ccgactttac caatgcttca cgtaccatga tatttgatat tcacaatctg     600
aagtgggatg accgtatgct ggacatcctt gatattccac gtgaaatgct gccagaagtt     660
aaagcatctt ctgaagttta cgggcagaca acatcggtg taaaggcgg aacccgtatt      720 ccgatcgccg ggatcgctgg tgatcagcag gcggctttat acggccagct ctgtgtgcaa     780
ccaggtatgg cgaagaatac gtatggtacc ggctgcttta tgttaatgaa taccggtaca     840
gaagcagtag cttctactca tggcctgctg acaacaattg cctgcggtcc acggggtgaa     900
gttaactatg cgctggaagg tgcagtcttt attggcggtg cttccattca atggctgcgt     960
gatgagatga aactgttctc tgaagcttta gactctgaat atttcgccac caaagtaaaa    1020
gactctaacg gggtttatat ggtgccggca tttaccggtt taggcgctcc gtactgggac    1080
ccatatgccc gtggagcaat ttttggcctg acccgcggaa ccaatgctaa ccatattatc    1140
cgcgctactc tggaatctat tgcctaccag actcgcgacg tgctggaagc aatgcagaat    1200
gatgcgaata cccgtctgca gtcattgcgg gtagatggtg gcgctgtggc gaataatttc    1260

-continued

```
ctgatgcaat tccagtccga tattctcgga acacgggttg agcgtccgga agttcgtgaa    1320
gtcaccgctc ttggagctgc ctatctggcc gggctggcag ttggattctg gaaagatctg    1380
gatgaagtcc gttcgaaagc ggttattgag cgcgagttcc gcccttcaat cgaaacgact    1440
gaacgtaact tccgttatgc cggctggaaa aaagctgttt cccgcgccct gcgctgggaa    1500
gatgaaaacg aacaataa                                                  1518
```

<210> SEQ ID NO 14
<211> LENGTH: 505
<212> TYPE: PRT
<213> ORGANISM: Pantoea citrea

<400> SEQUENCE: 14

```
Met Thr Asn Ala Glu Asn Lys Tyr Ile Val Ala Leu Asp Gln Gly Thr
 1               5                  10                  15

Thr Ser Ser Arg Ala Val Val Leu Asp His Asp Ala Asn Ile Ile Ala
                20                  25                  30

Val Ser Gln Arg Glu Phe Thr Gln His Tyr Pro Lys Thr Gly Trp Val
            35                  40                  45

Glu His Asp Pro Met Asp Ile Trp Ala Thr Gln Ser Ser Thr Leu Val
        50                  55                  60

Glu Val Leu Ala His Ala Asp Ile Arg Ser Asp Gln Ile Ala Ala Ile
65                  70                  75                  80

Gly Ile Thr Asn Gln Arg Glu Thr Thr Ile Val Trp Asp Lys Lys Thr
                85                  90                  95

Gly Lys Pro Val Tyr Asn Ala Ile Val Trp Gln Asp Pro Arg Thr Ala
            100                 105                 110

Asp Tyr Cys Ser Lys Leu Lys Lys Glu Gly Leu Glu Glu Tyr Ile Gln
        115                 120                 125

Lys Thr Thr Gly Leu Val Ile Asn Pro Tyr Phe Ser Gly Thr Lys Ile
    130                 135                 140

Lys Trp Ile Leu Asp Asn Val Glu Gly Ala Arg Asp Arg Ala Lys Arg
145                 150                 155                 160

Gly Glu Leu Leu Phe Gly Thr Val Asp Thr Trp Leu Val Trp Lys Met
                165                 170                 175

Thr Gln Gly Arg Val His Val Thr Asp Phe Thr Asn Ala Ser Arg Thr
            180                 185                 190

Met Ile Phe Asp Ile His Asn Leu Lys Trp Asp Asp Arg Met Leu Asp
        195                 200                 205

Ile Leu Asp Ile Pro Arg Glu Met Leu Pro Glu Val Lys Ala Ser Ser
    210                 215                 220

Glu Val Tyr Gly Gln Thr Asn Ile Gly Gly Lys Gly Gly Thr Arg Ile
225                 230                 235                 240

Pro Ile Ala Gly Ile Ala Gly Asp Gln Gln Ala Ala Leu Tyr Gly Gln
                245                 250                 255

Leu Cys Val Gln Pro Gly Met Ala Lys Asn Thr Tyr Gly Thr Gly Cys
            260                 265                 270

Phe Met Leu Met Asn Thr Gly Thr Glu Ala Val Ala Ser Thr His Gly
        275                 280                 285

Leu Leu Thr Thr Ile Ala Cys Gly Pro Arg Gly Glu Val Asn Tyr Ala
    290                 295                 300

Leu Glu Gly Ala Val Phe Ile Gly Gly Ala Ser Ile Gln Trp Leu Arg
305                 310                 315                 320
```

-continued

```
Asp Glu Met Lys Leu Phe Ser Glu Ala Leu Asp Ser Glu Tyr Phe Ala
            325                 330                 335

Thr Lys Val Lys Asp Ser Asn Gly Val Tyr Met Val Pro Ala Phe Thr
            340                 345                 350

Gly Leu Gly Ala Pro Tyr Trp Asp Pro Tyr Ala Arg Gly Ala Ile Phe
            355                 360                 365

Gly Leu Thr Arg Gly Thr Asn Ala Asn His Ile Ile Arg Ala Thr Leu
    370                 375                 380

Glu Ser Ile Ala Tyr Gln Thr Arg Asp Val Leu Glu Ala Met Gln Asn
385                 390                 395                 400

Asp Ala Asn Thr Arg Leu Gln Ser Leu Arg Val Asp Gly Gly Ala Val
            405                 410                 415

Ala Asn Asn Phe Leu Met Gln Phe Gln Ser Asp Ile Leu Gly Thr Arg
            420                 425                 430

Val Glu Arg Pro Glu Val Arg Glu Val Thr Ala Leu Gly Ala Ala Tyr
            435                 440                 445

Leu Ala Gly Leu Ala Val Gly Phe Trp Lys Asp Leu Asp Glu Val Arg
    450                 455                 460

Ser Lys Ala Val Ile Glu Arg Glu Phe Arg Pro Ser Ile Glu Thr Thr
465                 470                 475                 480

Glu Arg Asn Phe Arg Tyr Ala Gly Trp Lys Lys Ala Val Ser Arg Ala
            485                 490                 495

Leu Arg Trp Glu Asp Glu Asn Glu Gln
            500                 505
```

We claim:

1. A process for producing 2,5-diketo-D-gluconate (DKG) in a recombinant bacterial host cell comprising,
   a) culturing a *Pantoea citrea* host cell in the presence of glucose under conditions suitable for the production of 2,5-diketo-D-gluconate, wherein an endogenous polynucleotide of said *Pantoea citrea* host cell which encodes a glucokinase enzyme having at least 95% sequence identity with SEQ ID NO: 2 has been inactivated as a result of homologous recombination and
   b) producing DKG by the cultured *Pantoea citrea* host cell.

2. The process of claim 1 further comprising the step of recovering the DKG.

3. The process of claim 1 further comprising the step of converting the DKG to 2-keto-Lguionic acid by intracellular enzymatic conversion using said host cell.

4. A method of enhancing the production of 2,5-diketo-D-gluconate (DKG) from a carbon source comprising,
   a) obtaining an altered *Pantoea citrea* strain which comprises inactivating an endogenous glucokinase chromosomal gene in an unaltered *Pantoea citrea* host strain by homologous recombination, wherein the gene encodes a glucokinase having at least 95% sequence identity with SEQ ID NO: 2,
   b) culturing said altered *Pantoea citrea* stain under conditions suitable for the production of DKG, and
   c) allowing the production of DKG from the carbon source, wherein the production of said DKG is enhanced compared to the production of DKG in the unaltered *Pantoea citrea* host strain grown under essentially the same conditions.

5. A method of enhancing the production of 2,5-diketo-D-gluconate (DKG) from a carbon source in a *Pantoea citrea* cell comprising
   a) altering a *Pantoea citrea* host cell by
      (i) inactivating by homologous recombination a gene encoding an endogenous glucokinase enzyme having at least 95% sequence identity to SEQ ID NO: 2 and
      (ii) inactivating by homologous recombination a gene encoding an endogenous gluconokinase enzyme having at least 95% sequence identity to SEQ ID NO: 4,
   b) culturing the altered *Pantoea citrea* host cell under culture conditions suitable for the production of DKG, and
   c) allowing the production of DKG from a carbon source in the altered *Pantoea citrea* cell,
   wherein the production of DKG is enhanced in the altered *Pantoea citrea* cell compared to the production of DKG in a corresponding unaltered *Pantoea citrea* host cell grown under essentially the same culture conditions.

6. The method according to claim 5 further comprising recovering the DKG.

7. A method of enhancing the production of 2,5-diketo-D-gluconate (DKG) from a carbon source in a *Pantoea* cell comprising,
   a) altering a *Pantoea* host cell by inactivating a gene encoding an endogenous glucokinase enzyme by homologous recombination, said gene encoding a glucokinase having the amino acid sequence set forth in SEQ ID NO: 2;
   b) culturing the altered *Pantoea* host cell under culture conditions suitable for the production of DKG; and c) allowing the production of 2,5-diketo-D-gluconate from a carbon source in the altered *Pantoea* cell, wherein the production of the 2,5-diketo-D-gluconate is enhanced in the altered *Pantoea* cell compared to the production of 2,5-diketo-D-gluconate in a corresponding unaltered *Pantoea* host cell grown under essentially the same conditions.

8. The method according to claim 7, wherein the *Pantoea* cell is a *P. citrea* cell.

9. The method according to claim 7, wherein the endogenous glucokinase enzyme having the amino acid sequence of SEQ ID NO: 2 is encoded by a nucleic acid having the sequence of SEQ ID NO: 1.

10. The process of claim 1, wherein the endogenous glucokinase has at least 99% sequence identity to SEQ ID NO: 2.

11. The method according to claim 5 further comprising the step of converting the DKG to 2-keto-L-guionic acid by intracellular enzymatic conversion using said host cell.

12. The method according to claim 5, wherein the endogenous glucokinase has at least 99% sequence identity to SEQ ID NO: 2.

13. The method according to claim 5, wherein the endogenous gluconokinase has at least 99% sequence identity to SEQ ID NO: 4.

14. The method according to claim 4 further comprising the step of recovering the DKG.

15. The process according to claim 1, wherein art endogenous polynucleotide of said *Pantoea citrea* host cell which encodes a gluconokinase enzyme having at least 95% sequence identity with SEQ ID NO: 4 has been inactivated as a result of homologous recombination.

16. The process of claim 15, wherein the endogenous gluconokinase has at least 99% sequence identity to SEQ ID NO: 4.

* * * * *